United States Patent
Jones et al.

(10) Patent No.: US 9,943,313 B2
(45) Date of Patent: Apr. 17, 2018

(54) DETACHABLE COIL RELEASE SYSTEM AND HANDLE ASSEMBLY

(71) Applicants: Donald K. Jones, Dripping Springs, TX (US); Vladimir Mitelberg, Austin, TX (US)

(72) Inventors: Donald K. Jones, Dripping Springs, TX (US); Vladimir Mitelberg, Austin, TX (US)

(73) Assignee: Empirilon Technology LLC, Dripping Springs, TX (US)

(*) Notice: Subject to any disclaimer, the term of this patent is extended or adjusted under 35 U.S.C. 154(b) by 246 days.

(21) Appl. No.: 14/759,053

(22) PCT Filed: Jan. 2, 2014

(86) PCT No.: PCT/US2014/010099
§ 371 (c)(1),
(2) Date: Jul. 2, 2015

(87) PCT Pub. No.: WO2014/107529
PCT Pub. Date: Jul. 10, 2014

(65) Prior Publication Data
US 2015/0335333 A1 Nov. 26, 2015

Related U.S. Application Data

(60) Provisional application No. 61/748,534, filed on Jan. 3, 2013, provisional application No. 61/802,258, filed
(Continued)

(51) Int. Cl.
*A61M 29/00* (2006.01)
*A61B 17/12* (2006.01)
*A61B 17/00* (2006.01)

(52) U.S. Cl.
CPC .... *A61B 17/12109* (2013.01); *A61B 17/1214* (2013.01); *A61B 17/12145* (2013.01);
(Continued)

(58) Field of Classification Search
CPC .... A61B 17/12022; A61B 2017/12054; A61B 17/12154; A61B 17/12113;
(Continued)

(56) References Cited

U.S. PATENT DOCUMENTS

| 5,108,407 A | 4/1992 | Geremia et al. |
| 5,122,136 A | 6/1992 | Guglielmi et al. |

(Continued)

FOREIGN PATENT DOCUMENTS

| EP | 0832607 A1 | 4/1998 |
| EP | 1738698 A2 | 1/2007 |

(Continued)

OTHER PUBLICATIONS

PCT International Search Report for PCT/US14/010099, dated Jul. 7, 2015.*

*Primary Examiner* — Katherine M Shi
(74) *Attorney, Agent, or Firm* — Gordon & Jacobson, P.C.

(57) ABSTRACT

A medical implant deployment system for placing an implant at a preselected site comprising a deployment system that includes a mechanical coupling assembly at the distal end of a delivery member that engages the proximal end of the implant and a release member having an extended configuration in which the release member cooperatively maintains the coupling assembly engagement with the implant proximal end and a retracted configuration where the release member allows the coupling assembly to disengage from the implant proximal end. An attachable handle assembly is provided to place the release member in the (Continued)

retracted configuration allowing the coupling assembly to disengage from the implant proximal end, thereby releasing the implant.

44 Claims, 19 Drawing Sheets

Related U.S. Application Data on Mar. 15, 2013, provisional application No. 61/899,685, filed on Nov. 4, 2013.

(52) U.S. Cl.
CPC .................. *A61B 17/12154* (2013.01); *A61B 2017/00367* (2013.01); *A61B 2017/1205* (2013.01); *A61B 2017/12054* (2013.01)

(58) Field of Classification Search
CPC ...... A61B 17/1214; A61B 2017/00477; A61B 2017/00862; A61B 2017/1205; A61B 17/12109; A61B 17/12145; A61B 17/30; A61B 2017/00367; A61B 2017/12063; A61B 2017/12068; A61B 2017/12077; A61F 2002/9505; A61F 2002/9511; A61F 2/95
USPC ................................ 606/108, 200; 623/1.11
See application file for complete search history.

(56) References Cited

U.S. PATENT DOCUMENTS

| | | | |
|---|---|---|---|
| 5,250,071 | A | 10/1993 | Palermo |
| 5,261,916 | A | 11/1993 | Engelson |
| 5,263,964 | A | 11/1993 | Purdy |
| 5,334,210 | A | 8/1994 | Gianturco |
| 5,350,397 | A | 9/1994 | Palermo et al. |
| 5,382,259 | A | 1/1995 | Phelps et al. |
| 5,601,600 | A | 2/1997 | Ton |
| 5,746,769 | A | 5/1998 | Ton et al. |
| 5,895,391 | A | 4/1999 | Farnholtz |
| 7,179,276 | B2 | 2/2007 | Barry et al. |
| 7,779,842 | B1 * | 8/2010 | Russo ............... A61M 16/0463 128/205.19 |
| 2002/0120322 | A1 | 8/2002 | Thompson et al. |
| 2005/0154417 | A1 | 7/2005 | Sepetka et al. |
| 2008/0045997 | A1 | 2/2008 | Balgobin et al. |
| 2010/0004606 | A1 | 1/2010 | Hansen et al. |
| 2010/0030200 | A1 | 2/2010 | Strauss et al. |

FOREIGN PATENT DOCUMENTS

| | | |
|---|---|---|
| WO | WO2007/070792 A2 | 6/2007 |
| WO | WO2007/070797 A2 | 6/2007 |
| WO | WO2008/064205 A2 | 5/2008 |
| WO | WO2008/085606 A1 | 7/2008 |

* cited by examiner

DETACHABLE COIL RELEASE SYSTEM AND HANDLE ASSEMBLY

BACKGROUND OF THE INVENTION

For many years flexible catheters have been used to place various devices within the vessels of the human body. Such devices include dilatation balloons, radio-opaque fluids, liquid medications and various types of occlusion devices such as balloons and embolic coils. Examples of such catheter devices are disclosed in U.S. Pat. No. 5,108,407, entitled "Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils to preselected positions within vessels of the human body in order to treat aneurysms, or alternatively, to occlude the blood vessel at the particular location.

Coils which are placed in vessels may take the form of helically wound coils, or alternatively, may be random wound coils, coils wound within other coils or many other such configurations. Examples of various coil configurations are disclosed in U.S. Pat. No. 5,334,210, entitled, "Vascular Occlusion Assembly; U.S. Pat. No. 5,382,259, entitled, "Vasoocclusion Coil With Attached Tubular Woven Or Braided Fibrous Coverings." Embolic coils are generally formed of radiopaque metallic materials, such as platinum, gold, tungsten, or alloys of these metals. Often times, several coils are placed at a given location in order to occlude the flow of blood through the vessel by promoting thrombus formation at the particular location.

In the past, embolic coils have been placed within the distal end of the catheter. When the distal end of the catheter is properly positioned the coil may then be pushed out of the end of the catheter with, for example, a guidewire to release the coil at the desired location. This procedure of placement of the embolic coil is conducted under fluoroscopic visualization such that the movement of the coil through the vasculature of the body may be monitored and the coil may be placed at the desired location. With these placements systems there is very little control over the exact placement of the coil since the coil may be ejected to a position some distance beyond the end of the catheter.

Numerous procedures have been developed to enable more accurate positioning of coils within a vessel. Still another such procedure involves the use of a glue, or solder, for attaching the embolic coil to a guidewire which, is in turn, placed within a flexible catheter for positioning the coil within the vessel at a preselected position. Once the coil is at the desired position, the coil is restrained by the catheter and the guidewire is pulled from the proximal end of the catheter to thereby cause the coil to become detached from the guidewire and released from the catheter system. Such a coil positioning system is disclosed in U.S. Pat. No. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be very stiff with the result that it is very difficult to guide the catheter through the vasculature of the body.

Yet another coil deployment system is disclosed in U.S. Pat. No. 5,261,916, entitled, "Detachable Pusher-Vasoocclusive Coil Assembly with Interlocking Ball and Keyway Coupling." This system includes a pusher member with a tubular portion at its distal end that has a keyway for receiving the enlarged bead of an embolic coil through the outer wall and into the lumen of the tubular portion. The enlarged bead of the coil is positioned within the keyway and a resilient wire coupling the bead to the coil extends axially over the outer diameter of the distal end of the tubular portion to the remaining portion of the coil. The enlarged bead is retained in the keyway, forming an interlocking arrangement, by positioning the assembly within the lumen of an outer sleeve. Once the keyway is pushed from the confines of the sleeve the bead can disengage from the keyway. With this system the inner diameter has to be sufficiently large to accommodate the stack up of the wire coupled to the bead and the diameter of the tubular portion. Also when placing coils in an aneurysm "packed" with coils, there may not be enough room for the enlarged bead to disengage from the keyway.

Another coil release system is disclosed in U.S. Pat. No. 5,895,391 to Farnholtz, entitled, "Ball Lock Joint and Introducer for Vaso-occlusive Member". This system incorporates a tubular member having a portion of the wall cut away to receive at least a portion of an enlarged bead coupled to the proximal end of the embolic coil. A wire is placed within the lumen of the tubular member and cooperates to form an interference fit between the wire, bead and cut-away wall portion. To release the coil, the wire is pulled from the proximal end of the system to remove the interference fit with the bead and cut-away wall portion.

Still another coil deployment system utilizes a pair of jaws placed on the distal end of a pusher wire to position and release a coil. One such system is described in U.S. Pat. Nos. 5,601,600 and 5,746,769 to Ton et al., entitled, "Endoluminal Coil Delivery System Having A Mechanical Release Mechanism." Ton discloses an elongate pusher wire having jaws at the distal end. The jaws include tip projections which are perpendicular to the longitudinal axis of the pusher wire and when positioned with the lumen of a collar fixed to the proximal end of a coil, interlockingly engage with matching detents placed in the wall of the collar. A tubular body is used to slide over the pusher wire to collapse the jaws and release the collar. The disclosed interlocking engagement between the jaws and collar prevents forward and backwards axial movement of the jaws relative to the collar and allows any torqueing force applied to the jaws to be translated to the collar and affixed coil. Transmission of torque from a coil delivery system to a coil during the treatment of aneurysm may be detrimental to precise placement of the coil. The coils may coils store the torque energy and upon release from the delivery system, release the stored energy causing the coils to move unpredictably. Ton also states that jaws may be fixed to the coil, but does not provide or disclose any information as to how this may be accomplished.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate, relatively stiff element which extends throughout the length of the catheter with resulting stiffness of the catheter.

Another method for placing an embolic coil is that of utilizing a heat responsive coupling member which bonds the coil to the distal end of a delivery system. One such system uses electrical energy which is transmitted through electrical conductors to create heat which is applied to the coupling member to thereby soften and yield the coupling member in order to release the coil from the end of the delivery system. Such a method is disclosed in U.S. Pat. No. 7,179,276, entitled, "Heated Vascular Occlusion Coil Deployment System." Such a system suffers from the problem of having to pull an engagement member once the coupling is softened in order to release the coil.

BRIEF SUMMARY OF THE INVENTION

The present invention is directed toward a medical implant deployment system for use in placing a medical implant at a preselected site within the body of a mammal which includes an elongate delivery system having a coupling assembly at its distal end that releasably engages the proximal end of a medical implant. The delivery system includes an elongate tubular delivery member having proximal and distal ends, a coupling assembly positioned at the distal end of the delivery member and includes an engagement member and a tip member fixedly coupled to the distal end of engagement member. The coupling assembly is releasably coupled to the proximal end of an implant, such as an embolic coil, where the proximal end of the implant includes a coupling member having an aperture and an engagement portion. The engagement member of the coupling assembly is positioned within the aperture of the coupling member and the tip member of the engagement member engages the engagement portion of the coupling member. A release member having proximal and distal ends is positioned at the distal end of the delivery member, adjacent to the engagement member. The release member has a first configuration in which the distal end of the release member is positioned within the aperture of the coupling member and in cooperation with the engagement member, restricts the uncoupling of the engagement member from the coupling member. The release member also has a second configuration in which the distal end of the release member is removed from the aperture of the coupling member, thereby allowing the uncoupling of the engagement member from the coupling member.

The delivery system along with the distally located and releasably coupled medical implant is slidably positioned within the lumen of a catheter whose distal end is positioned adjacent a target implantation site. The delivery system is advanced such that the implant proximal end and coupling assembly distal end exit the lumen of the catheter. Once the implant is in the desired location, the release member is moved from its first configuration to its second configuration by proximal movement of the release member, relative to the delivery member, causing the distal end of the release member to be removed from the aperture of the coupling member, thus removing the cooperation previously restricting the uncoupling of the engagement member form the coupling member. With the release member in the second configuration, delivery system including the coupling assembly is moved proximally to insure the tip member of the engagement member is completely disengaged from the proximal end of the medical implant, thereby releasing the implant at the target site.

In accordance with one aspect of the present invention there is provided deployment system a having a generally tubular delivery member formed utilizing construction techniques well known in the formation of catheters or microcatheters. These construction techniques include for example braiding, coiling, extruding, laser cutting, joining, crimping, laminating, fusing and welding of components (such as markers bands, distal coil sections, tips and proximal sections) or portions of components to provide a delivery member having sufficient pushability, visibility and flexibility to traverse the anatomical tortuosity when accessing a target site in the body.

In accordance with another aspect of the present invention, there is provided a medical implant that takes the form of an embolization device such as an embolic or vasoocclusive coil for selective placement within a vessel, aneurysm, duct or other body location. Embolic coils are typically formed through the helical winding of a filament or wire to form an elongate primary coil. The wire or filament is typically a biocompatible material suitable for implantation and includes metals such as platinum, platinum alloys, stainless steel, nitinol and gold. Other biocompatible materials such as plastics groups including nylons, polyesters, polyolefins and fluoro-polymers may be processed to produce suitable filaments for forming coils. The wire usually has a circular cross-section, however, non-circular cross-sections, such as "D" shapes, are used in commercially available coils. The diameter of the wire may range from 0.0001" to about 0.010" and is largely dependent upon the particular clinical application for the coil. The diameter of the primary coil is generally dependent upon the wire diameter and the diameter of the mandrel used for winding. The primary coil diameter typically ranges from 0.002" to about 0.060" and is also dependent upon on the clinical application. The wound primary coil is typically removed from the mandrel leaving the coil with a lumen. In addition to the aforementioned method of winding a coil, there are other "mandrelless" forming processes that are suitable for making primary coils that plastically deform the wire into coil. The formed primary coils may be further processed to have a secondary shape such as a helix, sphere, "flower", spiral or other complex curved structure suited for implantation in a particular anatomical location. The secondary shape is imparted to the coil through thermal or mechanical means. Thermal means include forming the primary coil into a desired shape using a die or forming tool and then heat treating the coil to retain the secondary shape. Mechanical means include plastically deforming the primary coil into the desired shape or the use of a shaped resilient core wire inserted into the lumen of the primary coil to impart a shape to the coil. The length of the elongate primary coil range from 0.1 cm to about 150 cm with a preferred range of about 0.5 cm to about 70 cm. The distal end of the coil is typically rounded or beaded to make the coil end more atraumatic. Other variations of embolic coils suitable for use include stretch resistant coils, coils that incorporate a stretch resistant member(s) (within the coil lumen or exterior to the coil) that limits undesirable elongation of the primary coil during device manipulation and coated or modified coils that enhance occlusion through coils surface modifications, addition of therapeutics or volume filling materials (foams, hydrogels, etc.).

In accordance with still another aspect of the present invention there is provided an embolic coil deployment system that includes a tubular delivery member having proximal, intermediate and distal regions and comprises multiple zones of flexibility while minimizing the outer diameter profile and reducing the effects of compression and elongation when advancing and retracting the delivery member within a catheter. The tubular delivery member includes a proximal region preferably formed of a multi-filar single layer coil, an intermediate region preferably formed of a multi-filar, multi-layer coil and a distal region formed of a uni-filar coil. The regions of the delivery member may be joined together using known welding techniques including laser and resistance or may be brazed or soldered. The proximal and intermediate regions may alternatively incorporate metallic hypotubes to provide additional strength and minimize system elongation as well as the system profile. The distal region of the delivery member may also include radio opaque marker bands to align with the catheter during delivery and positioning of the embolic coil under fluoroscopy.

In accordance with yet another aspect of the present invention, the release member is positioned within the lumen of the delivery member and the proximal end of the release member extends proximal to the proximal region of the delivery member. The portion of the release member extending proximal to the proximal end of the delivery member may be grasped by a physician and moved proximally relative to the delivery member to move the release member from its first configuration to its second configuration during the release of an implant at the desired site.

In accordance with still yet another aspect of the present invention there is provided a delivery system that includes a proximal spring member positioned proximal to the proximal region of the delivery member. The proximal spring member has proximal and distal ends and is coaxially positioned about the proximal end of the release member such that the release member extends through the lumen of the proximal spring member. The proximal spring member distal end is coupled to the delivery member and the proximal end of the spring member coupled to the proximal end of the release member. The proximal spring member is preferably biased to maintain or place the release member in its first configuration in which the distal end of said release member is positioned within the aperture of the coupling member and in cooperation with the engagement member restrict the uncoupling of the engagement member from the coupling member of the implant. Proximal movement of the spring member proximal end relative to the delivery member causes the release member to move from its first configuration to its second configuration.

In accordance with still yet another aspect of the present invention there is provided a delivery system that includes an attachable handle assembly positioned at the proximal region of the delivery member. The handle assembly includes a housing body having first and second ends and a lumen extending therethrough and a plunger member having a top portion connected to an elongate shaft having a transverse lumen extending through the shaft. The housing body includes a channel positioned between the first and second ends and transversely intersects the housing lumen. The handle assembly has a first configuration in which the plunger shaft is positioned within the housing channel such that the transverse lumen of the plunger is coaxially aligned with the lumen of the housing. A centering tab on the plunger shaft engages with the housing body to preferentially maintain the handle assembly in its first configuration. Additionally, the handle assembly has a second configuration in which the plunger shaft position has been moved relative to the first configuration such that the shaft transverse lumen is offset from or no longer coaxially aligned with the housing lumen. To operate the handle assembly to release a medical implant, the proximal region of the delivery member is inserted into the handle assembly in its first configuration. More specifically the proximal spring member, which is coaxially disposed about the release member, is inserted into housing lumen at the first end such that it extends through the transverse lumen of the plunger shaft and into the housing lumen towards the housing second end. The plunger member of the handle assembly is then depressed and moved within the housing channel relative to the housing body, to displace the transverse shaft lumen relative to the housing lumen thereby stretching the proximal spring member and moving the release member proximally relative to the delivery member. As the handle assembly is placed in its second configuration, the release member is simultaneously placed in its second configuration thereby releasing the implant.

In accordance with an additional aspect of the present invention there is provided a delivery system that includes a tubular housing member that takes the form of a spring positioned at the distal region of the delivery member. The tubular housing member has proximal and distal ends and is coaxially positioned about the engagement member such that the engagement member extends through the lumen of the tubular housing member. The proximal ends of the housing member and the engagement member are fixedly coupled to the delivery member. The housing member preferably has a length such that the distal end of the housing member never extends distal to the tip member of the engagement member. Alternatively, the housing member may have a length in which the distal end of the housing member extends distal to the tip member of the engagement member when the release member is in its second configuration. While this alternative housing member length places the housing member in a slight state of compression, when the release member is in the first configuration and the tip member of the engagement member is engaged with the engagement portion of the coupling member, the compressed housing member may assist in the uncoupling of the tip member from the engagement portion of the coupling member when the release member is moved to its second configuration.

In accordance with another aspect of the present invention, there is provided a method of releasing a medical implant, such as an embolic coil, from a delivery system at a target site within the body including the steps of:

a) providing a medical implant system having a tubular delivery member releasably coupled to the proximal end of a medical implant where a release member in a first configuration and an engagement member having a distal tip member are positioned within an aperture of the implant and cooperatively maintain engagement with the implant distal to the distal end of the tubular delivery member;

b) inserting the medical implant coupled to the delivery member into the lumen of a catheter;

c) advancing the delivery member and implant through the catheter lumen to the catheter distal end;

d) positioning the implant at a target site within the body;

e) operating the release member to move the release member from the first configuration to a second configuration in which the release member is moved proximally thereby withdrawing the distal end of the release member from the aperture of the implant; and f) releasing the implant at the target site by moving the delivery member proximally such that the engagement member is removed from the aperture of the implant.

This method may include additional modifications in which step e) is performed by first: inserting the delivery member proximal region having a proximal spring member coupled to the release member into a handle assembly; and operating the handle assembly to move the release member from the first configuration to a second configuration in which the release member is moved proximally thereby withdrawing the distal end of the release member from the aperture of the implant.

In accordance with yet another aspect of the present invention, there is provided a method of coupling a medical implant such as an embolic coil to a delivery member comprising the steps of:

a) providing a medical implant having a coupling member at its proximal end where the coupling member has an aperture and an engagement portion;

b) providing a tubular delivery member having at its distal end an engagement member with a distally located tip member and an elongate release member positioned in the lumen of the tubular delivery member;

c) inserting the engagement member within the aperture of the implant coupling member such that the tip member is adjacent the engagement portion of the coupling member; and d) operating the release member to move the release member from a second configuration in which the release member does not restrict the tip member from being withdrawn through the aperture to a first configuration in which the release member distal end is positioned within the coupling member aperture adjacent the engagement member to cooperatively maintain secure engagement with the implant distal to the distal end of the tubular delivery member.

These aspects of the invention and the advantages thereof will be more clearly understood from the following description and drawings of embodiments of the present invention:

DETAILED DESCRIPTION OF THE INVENTION

Figure 1:
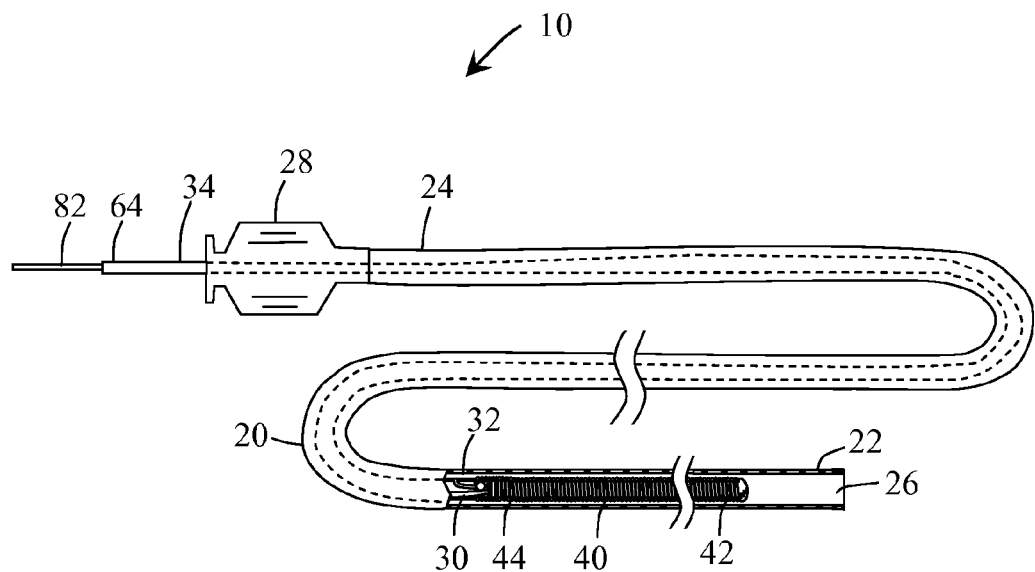
FIG. 1 is a partially sectioned view of an embolic coil deployment system according to an embodiment of the present invention.

Generally, a medical implant deployment system of the present invention may be used to position an implant at a preselected site within the body of a mammal. The medical implant deployment system may be used to place various implants such as stents and embolization coils. FIG. 1 generally illustrates a medical implant deployment system 10 according to an embodiment of the present invention which includes delivery catheter 20 having a distal end 22, a proximal end 24, a lumen 26 extending therethrough and a catheter hub 28 affixed to proximal end 24, a delivery system 30 having a distal end 32 and a proximal end 34 and an embolic coil 40 having a distal end 42 and a proximal end 44 that is releasably coupled to the distal end 32 of delivery system 30. Embolic coil 40 is a medical implant of a general type suitable for use in occluding a vessel, duct or aneurysm.

Embolic coil 40 is generally formed from a primary coil of a helically wound wire 41, made from a material which is biocompatible and preferably radio-opaque. Suitable biocompatible materials include metals such as platinum, platinum alloys, stainless steel, nitinol, tantalum and gold and plastics such as nylons, polyesters, polyolefins and fluoropolymers. The wire usually has a circular cross-section, however, non-circular cross-sections, such as "D" shapes, are used in commercially available coils. The diameter of the wire may range from 0.0001" to about 0.010" and is largely dependent upon the particular clinical application for the coil. The diameter of the primary coil is generally dependent upon the wire diameter and the diameter of the mandrel used for winding. The primary coil diameter typically ranges from 0.002" to about 0.060" and is also dependent upon on the clinical application. The wound primary coil is typically removed from the mandrel leaving the coil with a lumen 45. In addition to the aforementioned method of winding a coil, there are other "mandrel-less" forming processes that are suitable for making primary coils that plastically deform the wire into coil. The formed primary coils may be further processed to have a secondary shape such as a helix, sphere, "flower", spiral or other complex curved structure suited for implantation in a particular anatomical location. The secondary shape is imparted to the coil through thermal or mechanical means. Thermal means include forming the primary coil into a desired shape using a die or forming tool and then heat treating the coil to retain the secondary shape. Mechanical means include plastically deforming the primary coil into the desired shape or the use of a shaped resilient core wire inserted into the lumen of the primary coil to impart a shape to the coil. The length of the elongate primary coil ranges from 0.1 cm to about 150 cm with a preferred range of about 0.5 cm to about 70 cm. The distal end of the coil is typically rounded or beaded to make the coil end more atraumatic. Other variations of embolic coils suitable for use include stretch resistant coils, coils that incorporate a stretch resistant member(s) (within the coil lumen or exterior to the coil) that limits undesirable elongation of the primary coil during device manipulation and coated or modified coils that enhance occlusion through coils surface modifications, addition of therapeutics or volume filling materials (foams, hydrogels, etc.).

Figure 2:
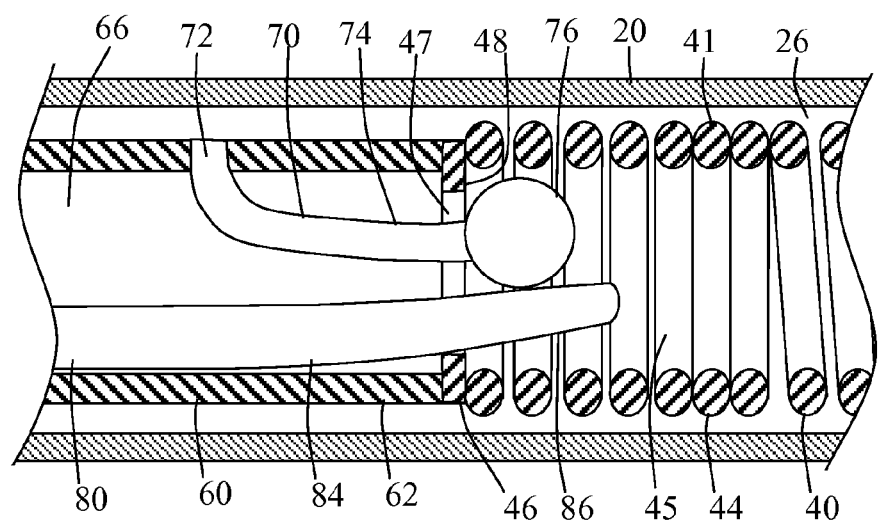
FIG. 2 is an enlarged partially sectioned view showing a distal portion of the embolic coil deployment system of FIG. 1.

FIG. 2 illustrates in more detail the construction of the implant deployment system 10 with the implant, coil 40, being positioned within catheter lumen 26 at catheter distal end 22. Embolic coil 40 includes a headpiece coupling member 46 positioned at coil proximal end 44. Headpiece coupling member 46 includes an aperture 47 and an engagement portion 48. Delivery system 30 includes a tubular delivery member 60 having a distal end 62, a proximal end 64 and a lumen 66 extending therethrough. Delivery member 60 maybe formed utilizing construction techniques well known in the formation of catheters or microcatheters. These construction techniques include for example braiding, coiling, extruding, laser cutting, joining, crimping, laminating, fusing and welding of components (such as markers bands, distal coil sections, tips and proximal sections) or portions of components to provide a delivery member having sufficient pushability, visibility and flexibility to traverse the luminal tortuosity when accessing an intended implantation site. Delivery system 30 also includes an engagement member 70 having a proximal end 72, a distal end 74 and a tip member 76 coupled to distal end 74. Tip member 76 preferably takes the form of a generally spherical bead, however, shapes such as rounded disks and other curvilinear geometries that allow the tip member to easily disengage from the engagement portion of the implant coupling member may also be suitable. Engagement member 70 is shown positioned at the distal end 62 of delivery member 60 and secured to delivery member 60 preferably by laser welding but may take the form of any suitable joining technique such as soldering, spot welding, adhesives and ultrasonic welding. Delivery system 30 also includes an elongate release member 80 having a proximal end 82, a distal end 84 and a tip portion 86. Release member 80 preferably takes the form of an elongate resilient nitinol wire although other materials and forms such as tubes or cables may be suitable. Release member 80 is positioned within the lumen 66 of delivery member 60 where the proximal end 82 extends proximal to proximal end 64.

As previously discussed, the proximal end 44 of embolic coil 40 is releasably coupled to the distal end 32 of delivery system 30. More particularly, delivery member distal end 62 and engagement member 70 engage coupling member 46 positioned at coil proximal end 44. As shown in FIG. 2, the distal end 74 of engagement member 70 is positioned within aperture 47 of coupling member 46. Aperture 47 has a diameter larger than the diameter of tip member 76, thereby allowing tip member 76 to be easily inserted into or removed from coupling member 46. In a first configuration, distal end 84 of release member 80 is positioned within aperture 47 of coupling member 46 adjacent to engagement member distal end 74, while tip member 76 positioned through aperture 47, is engaged with engagement portion 48. The diameters of release member distal end 84 and engagement member distal end 74 cooperatively restrict tip member 76 from being withdrawn through aperture 47. While in this configuration, coil proximal end 44 is securely coupled to delivery member distal end 62 and allows delivery member 60 to advance or retract embolic coil 40 within the catheter.

Figure 3A:
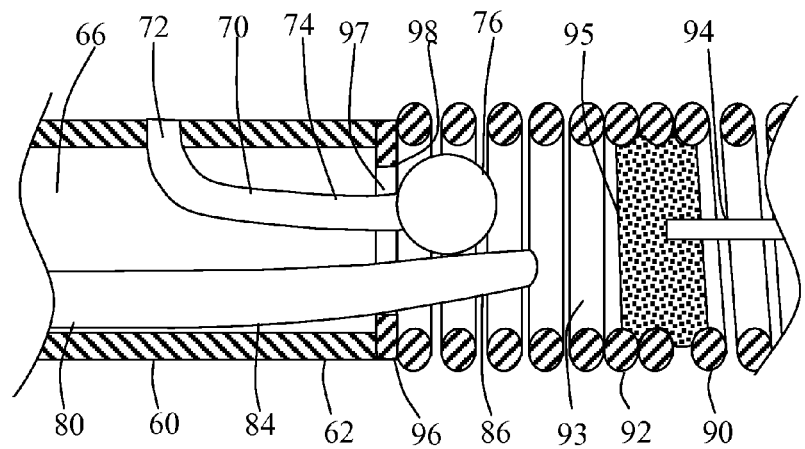
FIG. 3A is a partial perspective view of the delivery system distal end coupled to a stretch resistant embolic coil according to another embodiment of the present invention.

FIG. 3A illustrates a partial perspective view of delivery member 60 coupled to alternatively constructed embolic coil 90 according to another embodiment of the present invention. Embolic coil 90 has a distal end 91 (not shown), a proximal end 92 and a lumen 93 extending therethrough. An elongate stretch resistant member 94 is positioned within lumen 93 and extends from proximal end 92 to distal end 91. Stretch resistant member 94, preferably takes the form of a filamentous metallic wire having a small diameter ranging from about 0.0001" to about 0.003", however other materials such as polymers, glass and ceramics that provide both flexibility and appropriate stretch resistant characteristics, that limits undesirable elongation of coil 90 during device manipulation, may also be suitable. The distal end of stretch resistant member 94 is fixedly coupled distally to distal end 91. The proximal end of stretch resistant member 94 is fixedly coupled at proximal end 92 by securing region 95. Securing region 95 is preferably a weld region, however other joining methods utilizing solder or adhesives are also suitable. Like the aforementioned embolic coil embodiment, embolic coil 90 has a proximal end 92 that includes a coupling member 96 having an aperture 97 and an engagement portion 98. Engagement member distal end 74 is positioned within aperture 97 adjacent release member distal end 84. Engagement member distal end 74 and release member distal end 84 cooperate to restrict tip member 76 from being withdrawn through aperture 97 thereby maintaining the secure coupling of embolic coil 90 with delivery member 60.

Figure 3B:
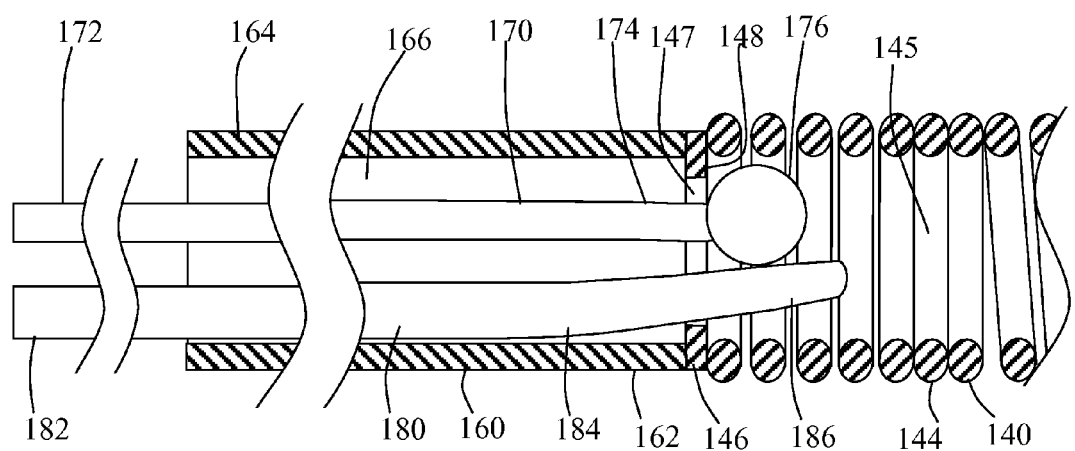
FIG. 3B is a partial perspective view of a delivery system according to another embodiment of the present invention.

FIG. 3B illustrates a partial perspective view of an embolic coil 140 coupled to an alternative delivery member 160 according to another embodiment of the present invention. Embolic coil 140 has a distal end 142 (not shown), a proximal end 144 and a lumen 145 extending therethrough. Like the aforementioned embolic coil embodiments, embolic coil 145 has a proximal end 144 that includes a coupling member 146 having an aperture 147 and an engagement portion 148. Similarly, delivery member 160 has distal and proximal ends 162 and 164 respectively, and a lumen 166 extending therethrough. An elongate engagement member 170 having a proximal end 172, a distal end 174 and a tip member 176 is slidably positioned within lumen 166 of delivery member 160. Proximal end 172 of engagement member 170 extends proximal to delivery member proximal end 164. Also positioned within lumen 166 is an elongate release member 180 having a proximal end 182, a distal end 184 and a tip portion 186. Delivery member 160 is coupled to embolic coil 140 such that distal end 162 of the delivery member is adjacent coupling member 146 of the embolic coil. More particularly, engagement member distal end 174 is positioned within aperture 147 and tip member 176 is adjacent engagement portion 148. Release member 180 is show in a first configuration where distal end 184 is positioned adjacent engagement member distal end 174 within aperture 147. In this first configuration, engagement member distal end 174 and release member distal end 184 cooperate to restrict tip member 176 from being withdrawn through aperture 147 thereby maintaining the secure coupling of embolic coil 140 with delivery member 160. To release the embolic coil from the delivery member, release member 180 is placed in a second configuration where proximal end 182 is moved proximally relative to delivery member 160, causing distal end 184 to be withdrawn from aperture 147. With release member 180 in the second configuration, tip member 176 is no longer restricted from moving proximally through aperture 147 and may be withdrawn from coupling member 146 by moving engagement member 170 proximally relative to coil proximal end 144 thereby releasing embolic coil 140.

Figure 4:
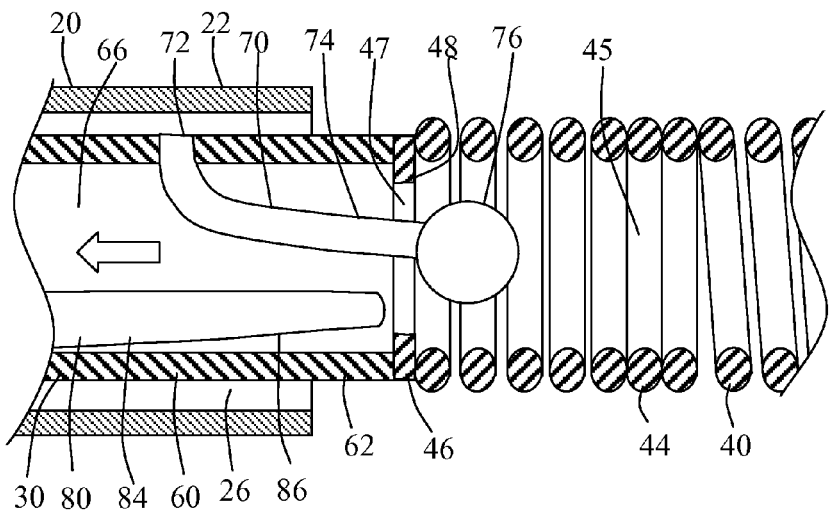
FIG. 4 is a partially sectioned view of the delivery system distal end engaged with an embolic coil where the release member is moved proximally relative to the coil.
Figure 5:
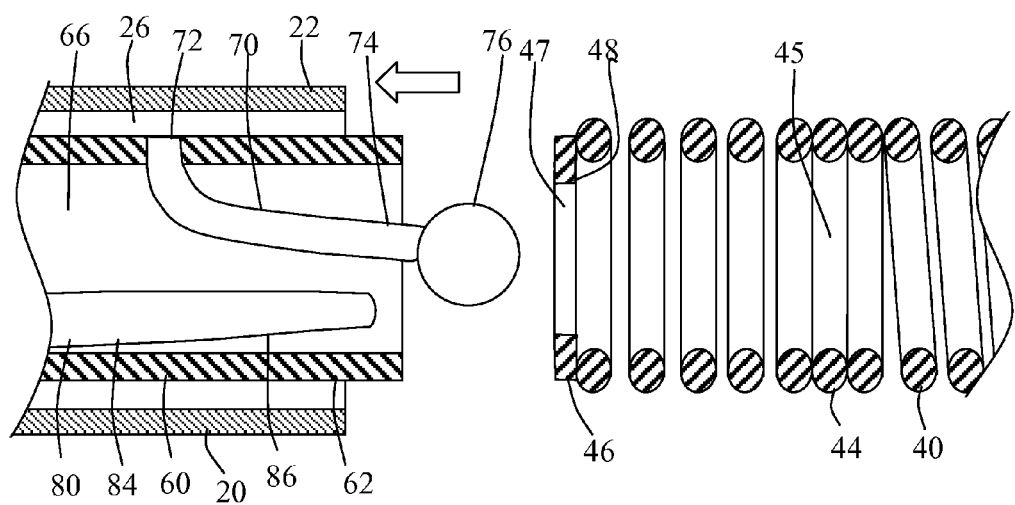
FIG. 5 is a partially sectioned view of the delivery system distal end moved proximally to release the embolic coil.

FIGS. 4 and 5 illustrate various relative positions of delivery system 30 and proximal end 44 of embolic coil 40 for clarification and discussion regarding the release of coil 40 from delivery system 30. FIG. 4 depicts delivery system 30 where distal end 62 of delivery member 60 has exited catheter lumen 26 at distal end 22 and coil 40 has been properly positioned at a target site. Release member 80 is shown moving from its first configuration to a second configuration by moving the release member proximal end 82 proximally relative to the delivery member proximal end 64, such that distal end 84 and tip portion 86 are withdrawn from aperture 47 of coupling member 46. With release member 80 in its second configuration, tip member 76 of engagement member 70 is no longer restricted from being withdrawn through aperture 47 although delivery member 60 may still be coupled to embolic coil 40. As shown in FIG. 5, delivery member distal end 62 is moved proximally withdrawing distal end 74 and tip member 76 of engagement member 70 from aperture 47 of coupling member 46, thereby releasing embolic coil 40 at the target site.

Figure 6:
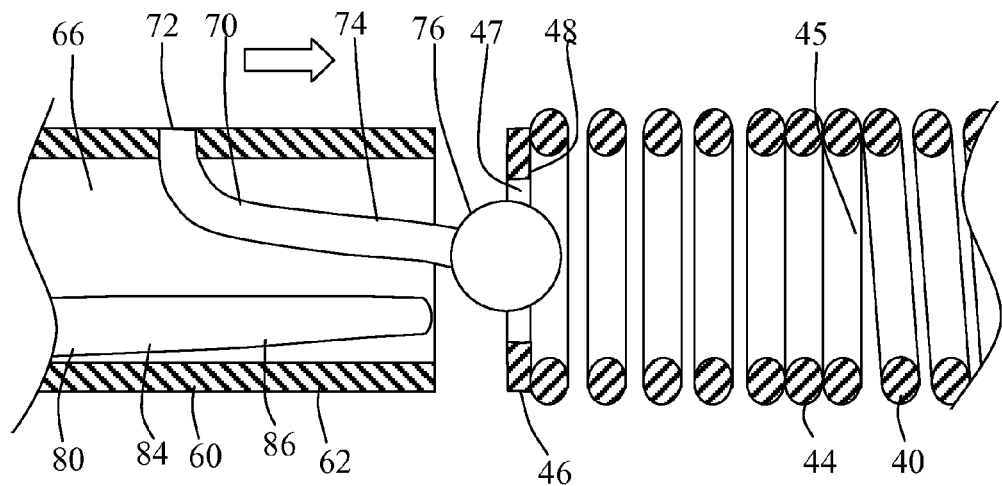
FIG. 6 is a partially sectioned view of the delivery system distal end moved distally to engage an embolic coil proximal end.
Figure 7:
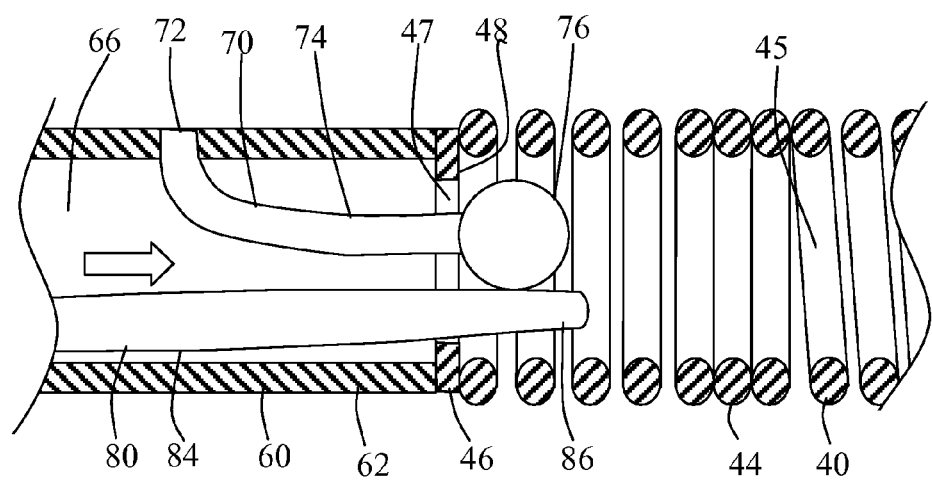
FIG. 7 is a partially sectioned view of the delivery system distal end engaging an embolic coil proximal end where the release wire is moved distally and positioned to restrict uncoupling.

FIGS. 6 and 7 generally illustrate method steps for the coupling of delivery system 30 to embolic coil 40 according to an embodiment of the present invention. FIG. 6 shows delivery member distal end 62 being moved distally towards the proximal end 44 of embolic coil 40. More particularly, tip member 76 and distal end 74 of engagement member 70 is inserted into aperture 47 of coupling member 46. With tip member 76 positioned through aperture 47 adjacent engagement portion 48, release member 80 is advanced distally (by moving proximal end 82 distally relative to delivery member proximal end 64) from its second configuration in which release member 80 does not restrict tip member 76 from being withdrawn through aperture 47 to a first configuration in which the release member distal end 84 is positioned within coupling member aperture 47 adjacent to engagement member 70 to cooperatively maintain secure engagement with coil proximal end 44 distal to distal end 62 of tubular delivery member 60. While release member 80 is in its first configuration, delivery member 60 and embolic coil 40 are securely coupled to allow introduction and delivery of the coil through a catheter in addition to the positioning and subsequent release of the coil at a target site within the body.

Figure 8:
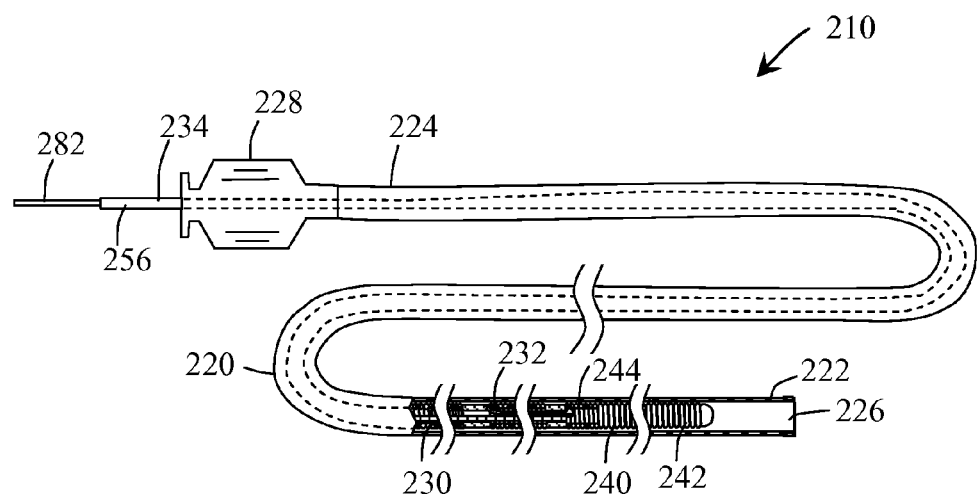
FIG. 8 is a partially sectioned view of an embolic coil deployment system according to another embodiment of the present invention.

FIG. 8 generally illustrates a medical implant deployment system 210 according to another embodiment of the present invention which includes delivery catheter 220 having a distal end 222, a proximal end 224, a lumen 226 extending therethrough and a catheter hub 228 affixed to proximal end 224, a delivery system 230 having a distal end 232 and a proximal end 234 and an embolic coil 240 having a distal end 242 and a proximal end 244 that is releasably coupled to the distal end 232 of delivery system 230. Embolic coil 240 is a medical implant of a general type suitable for use in occluding a vessel, lumen, duct or aneurysm.

Embolic coil 240 is generally formed from a primary coil of a helically wound wire 41, made from a material which is biocompatible and preferably radio-opaque. Suitable biocompatible materials include metals such as platinum, platinum alloys, stainless steel, nitinol, tantalum and gold and plastics such as nylons, polyesters, polyolefins and fluoropolymers. The wire usually has a circular cross-section, however, non-circular cross-sections, such as "D" shapes, are used in commercially available coils. The diameter of the wire may range from 0.0001" to about 0.010" and is largely dependent upon the particular clinical application for the coil. The diameter of the primary coil is generally dependent upon the wire diameter and the diameter of the mandrel used for winding. The primary coil diameter typically ranges from 0.002" to about 0.060" and is also dependent upon on the clinical application. The wound primary coil is typically removed from the mandrel leaving the coil with a lumen 245. In addition to the aforementioned method of winding a coil, there are other "mandrel-less" forming processes that are suitable for making primary coils that plastically deform the wire into coil. The formed primary coils may be further processed to have a secondary shape such as a helix, sphere, "flower", spiral or other complex curved structure suited for implantation in a particular anatomical location. The secondary shape is imparted to the coil through thermal and or mechanical means. Thermal means include forming the primary coil into a desired shape using a die or forming tool and then heat treating the coil to retain the secondary shape. Mechanical means include plastically deforming the primary coil into the desired shape or the use of a shaped resilient core wire inserted into the lumen of the primary coil to impart a shape to the coil. The length of the elongate primary coil ranges from 0.1 cm to about 150 cm with a preferred range of about 0.5 cm to about 70 cm. The distal end of the coil is typically rounded or beaded to make the coil end more atraumatic. Other variations of embolic coils suitable for use include stretch resistant coils, coils that incorporate a stretch resistant member(s) (within the coil lumen or exterior to the coil) that limit undesirable elongation of the primary coil during device manipulation and coated or modified coils that enhance occlusion through coils surface modifications, addition of therapeutics or volume filling materials (foams, hydrogels, etc.).

Figure 9:
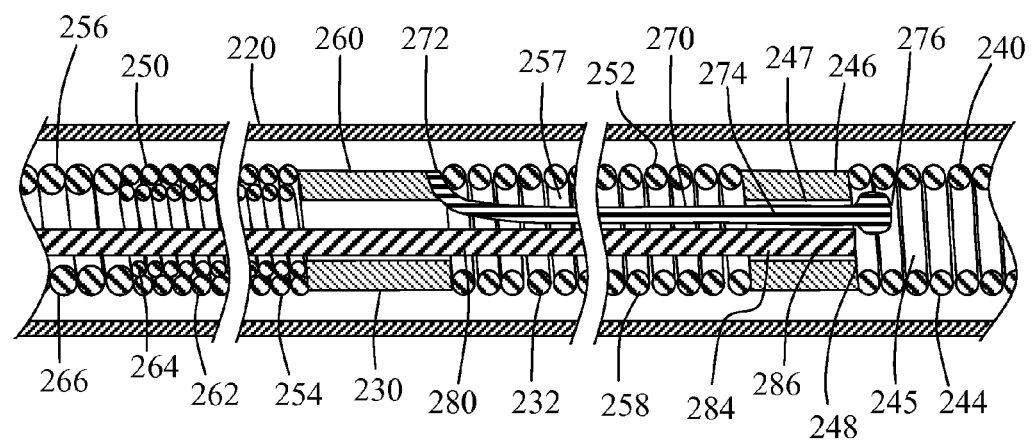
FIG. 9 is an enlarged partially sectioned view showing a distal portion of the embolic coil deployment system of FIG. 8.

FIG. 9 illustrates in more detail the construction of the implant deployment system 210 with the implant, coil 240, being positioned within lumen 226 of catheter 220. Embolic coil 240 includes a headpiece coupling member 246 positioned at coil proximal end 244. Headpiece coupling member 246 includes an aperture 247 and an engagement portion 248. Delivery system 230 includes a tubular delivery member 250 having a distal region 252, an intermediate region 254, a proximal region 256 and a lumen 257 extending therethrough. Distal region 252 of delivery member 250 preferably takes the form of a helically wound coil 258 having a wire diameter ranging from 0.0005 in to 0.006 in and a preferred wire diameter range of about 0.001 in to 0.003 in. Distal region 252 has an axial length that ranges from about 1 cm to about 10 cm and preferably ranges from about 2.5 cm to about 3.5 cm. Tubular marker band 260 is coupled to the proximal portion of coil 258. Intermediate region 254 of delivery member 250 preferably takes the form of a multi-filar wound coil having an outer coil 262 having a number of filaments ranging from 5 to 12 and with filament diameters ranging from 0.001 in to 0.005 in and a preferred number of filaments ranging from 6 to 8 and preferred filament diameters between about 0.0015 in and 0.0035 in and an inner coil 264 having a number of filaments ranging from 5 to 12 and with filament diameters ranging from 0.001 in to 0.005 in and a preferred number of filaments ranging from 6 to 8 and preferred filament diameters between about 0.0015 in and 0.0035 in. Intermediate region 254 has an axial length that ranges from about 20 cm to about 50 cm and preferably ranges from about 30 cm to about 40 cm. The distal ends of intermediate region coils 262 and 264 are preferably welded to the proximal end of marker band 260. Proximal region 256 of delivery member 250 preferably takes the form of a multi-filar wound coil 266 having a number of filaments ranging from 5 to 12 and with filament diameters ranging from 0.002 in to 0.006 in and a preferred number of filaments ranging from 6 to 8 and preferred filament diameters of about 0.003 to 0.005 in. Proximal region 256 has an axial length that ranges from about 120 cm to about 170 cm and preferably ranges from about 140 cm to about 160 cm. The distal end of coil 266 is preferably welded to the proximal end of intermediate region 254. While the aforementioned distal, intermediate, proximal regions of delivery member 250 are presented with their respective preferred forms to produce a delivery member having a small diameter profile, these regions of delivery member 250 may also take the form of components used in the construction of catheters and microcatheters, that include laser cut hypotubes, standard hypotubes, braided materials, tubular polymer materials and composites.

Delivery system 230 also includes an engagement member 270 having a proximal end 272, a distal end 274 and a tip member 276 coupled to distal end 274. Tip member 276 preferably takes the form of a generally spherical bead, however, shapes such as rounded disks and other curvilinear geometries that allow the tip member to easily disengage from the engagement portion of the implant coupling member may also be suitable. Engagement member 270 is shown positioned at the distal region 252 of delivery member 250 and secured to delivery member 250 preferably by laser welding but may take the form of any suitable joining technique such as soldering, spot welding, adhesives and ultrasonic welding. Delivery system 230 also includes an elongate release member 280 having a proximal end 282, a distal end 284 and a tip portion 286. Release member 280 preferably takes the form of an elongate resilient nitinol wire although other materials such as stainless steel, platinum alloys, glass or ceramic fibers, polymeric fibers, etc. and forms such as tubes or cables may be suitable. Release member 280 typically has a length which is longer than the combined lengths of the distal, intermediate and proximal regions of delivery system 230. Release member 280 is positioned within lumen 257 of delivery member 250 where the proximal end 282 extends proximal to proximal region 256.

As previously discussed, the proximal end 244 of embolic coil 240 is releasably coupled to the distal end 232 of delivery system 230. More particularly, delivery member distal region 252 and engagement member 270 engage coupling member 246 positioned at coil proximal end 244.

As shown in FIG. 9, the distal end 274 of engagement member 270 is positioned within aperture 247 of coupling member 246. Aperture 247 has a diameter larger than the diameter of tip member 276, thereby allowing tip member 276 to be easily inserted into or removed from coupling member 246. In a first configuration, distal end 284 of release member 280 is positioned within aperture 247 of coupling member 246 adjacent to engagement member distal end 274, while tip member 276, positioned through aperture 247, is engaged with engagement portion 248. The diameters of release member distal end 284 and engagement member distal end 274 cooperatively restrict tip member 276 from being withdrawn through aperture 247. While in this configuration, coil proximal end 244 is securely coupled to delivery member distal region 252 and allows delivery member 250 to advance or retract embolic coil 240 within the catheter.

Figure 10A:
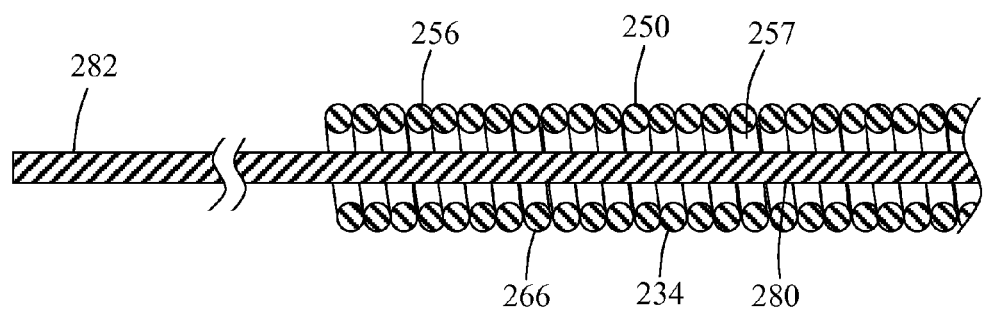
FIG. 10A is a partially sectioned view showing a proximal portion of the embolic coil deployment system of FIG. 8 according to an embodiment of the present invention.
Figure 10B:
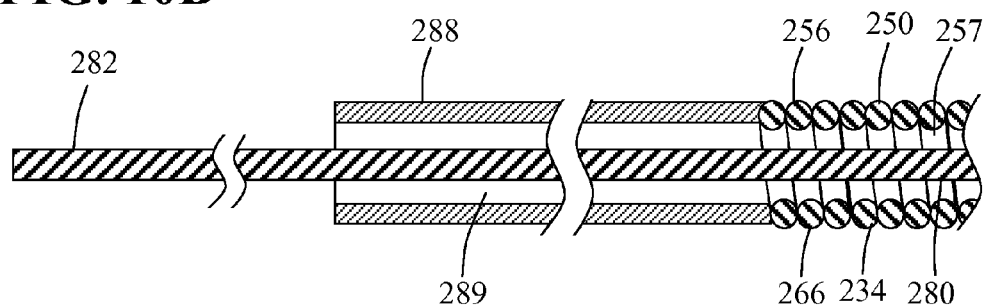
FIG. 10B is a partially sectioned view showing a proximal portion of the embolic coil deployment system of FIG. 8 according to another embodiment of the present invention.
Figure 10C:
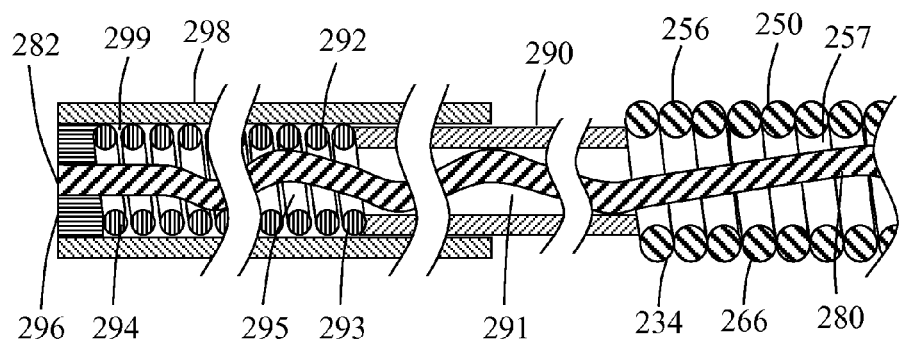
FIG. 10C is a partially sectioned view showing a proximal portion of the embolic coil deployment system of FIG. 8 according to yet another embodiment of the present invention.

Several embodiments of the proximal region 256 of delivery member 250 are shown in FIGS. 10A through 10C. FIG. 10A illustrates a first embodiment of proximal region 256 of delivery member 250 in which release member 280 is shown positioned within lumen 257. Release member 280 extends proximally from coil 266 such that release member proximal end 282 exits lumen 257.

According to a second embodiment, proximal region 256 of delivery member 250 includes a shaft portion 288 coupled to the proximal end of coil 266 as shown in FIG. 10B. Shaft portion 288 preferably takes the form of a hypotube having a stiffness which is greater than that of the distal region of delivery member 250. Lumen 257 of delivery member 250 is contiguous with lumen 289 of shaft portion 288. In this embodiment, release member 280 extends proximally from coil 266 and through the lumen of shaft portion 288 such that release member proximal end 282 exits lumen 257.

FIG. 10C illustrates a third embodiment of the proximal region 256 of delivery member 250 which includes shaft portion 290 coupled to the proximal end of coil 266. Shaft portion 290 preferably takes the form of a hypotube having a through lumen 291 and a stiffness which is greater than that of the distal region of delivery member 250. Coupled to the proximal end of shaft portion 290 is release member coil 292 having distal end 293, proximal end 294 and lumen 295. Distal end 293 is fixedly coupled to the proximal end of shaft 290 preferably by welding however other joining methods may be suitable. Release member 280 extends proximally from coil 266 through lumen 291 of shaft portion 290 and into lumen 295 of release member coil 292. The proximal end 282 of release member 280 is fixedly coupled to release member coil proximal end 294 by joint member 296. Joint member 296 preferably takes to form of a weld joint; however, other joining techniques such as solder, adhesives or mechanical interlocks may also be suitable. Release member coil 292 is preferably formed of a resilient material, such as stainless steel and is capable of being stretched (elastically and or plastically) from an initial length configuration to an extended length configuration. The length of release member coil 292 in its initial configuration ranges from about 1 to 15 cm and preferably ranges from about 2 to 5 cm. Release member coil 292 is preferably secured to release member proximal end 282 during assembly when coil 292 is in an extended configuration (and within the elastic limits) such that when the coil returns to its initial configuration it applies a distally directed force to release member 280 relative to delivery member 250. This distally directed force ensures that release member 280 is in its first configuration, where the release member distal end 284 is in an appropriate position relative to engagement member 274 within coupling member 246 to maintain the cooperative arrangement securely coupling embolic coil 240 to delivery member 250 during the advancement of delivery member 250 through a catheter positioned in tortuous anatomy.

The first and second embodiments of the proximal region 256 of delivery member 250 shown in FIGS. 10A and 10B depict proximal end 282 of release member 280 extending from lumens 257 and 289, which are unshielded by other members. The unshielded or exposed portions of release member proximal end 282 generally have a length that facilitates grasping proximal end 282 by a physician to move release member 280 proximally, relative to delivery member 250, from its first configuration to its second configuration. The third embodiment of the proximal region 256 of delivery member 250 shown in FIG. 10C depicts proximal end 282 of release member 280 positioned within lumen 295 which is thusly shielded by release member coil 292. The shielding of proximal end 282 by release member coil 292 minimizes likelihood of inadvertent actuation of release member 280 that could cause premature release of a secured embolic coil. As shown in FIG. 10C, additional shielding to further minimize inadvertent actuation of release member 280 may be provided by including tubular outer member 298 having lumen 299. Release member coil 292 is positioned within lumen 299 of outer member 298 and outer member 298 is coupled to release member proximal end 282. Outer member 298 preferably takes the form of a metallic stainless steel hypotube however other materials such as polymers or ceramics may be suitable. Coupling outer member 298 to release member proximal end 282 may be accomplished by welding outer member 298 to joint member 296. Alternatively, outer member 298 may take the form of a polymer tube that has been thermally processed to engage release member coil proximal end 294 and or joint member 296, while allowing outer member 298 to move axially relative to release member coil distal end 293. Additionally, the distal end of outer member 298 may also be thermally processed to shrink and create a frictional engagement with the proximal end of shaft 290 to thereby minimize inadvertent stretching of release coil 292 during handling.

Figure 11:
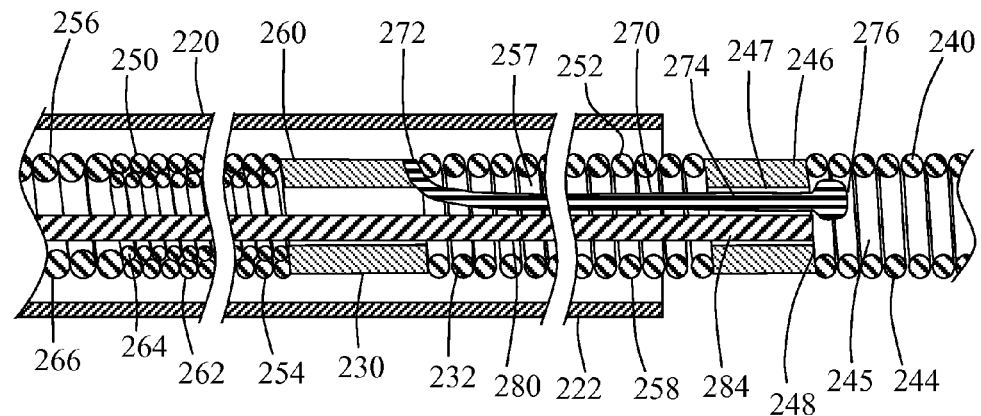
FIG. 11 is a partially sectioned view of the distal region of the embolic coil deployment system showing embolic coil exiting the catheter distal end.

The general procedure for delivering a medical implant to target site within the body according to an embodiment of the present invention includes positioning a catheter within the body such that the tip of the catheter is adjacent a target anatomical site. Delivery system 230 and securely coupled embolic coil 240 are then introduced into the catheter lumen at the catheter proximal end and is advanced distally through catheter 220. The distal end of embolic coil 240 exits the lumen at the distal end of the catheter adjacent the target site. Further distal advancement of delivery system 230 allows embolic coil to be deployed from the catheter lumen. If desired delivery system 230 may be retracted and advanced to provide the desired positioning of embolic coil 240 at the target site. Once proper positioning of embolic coil 240 has been achieved, coupling member 246 of the embolic coil should be positioned just distal to the catheter distal end. This can be achieved under fluoroscopy by aligning radiopaque markers on the delivery system with radiopaque markers on the catheter. FIG. 11 illustrates the relative positions of the catheter distal end 222, delivery system 230 and the embolic coil proximal end 244 prior to the release of embolic coil 240 from delivery system 230.

Figure 12A:
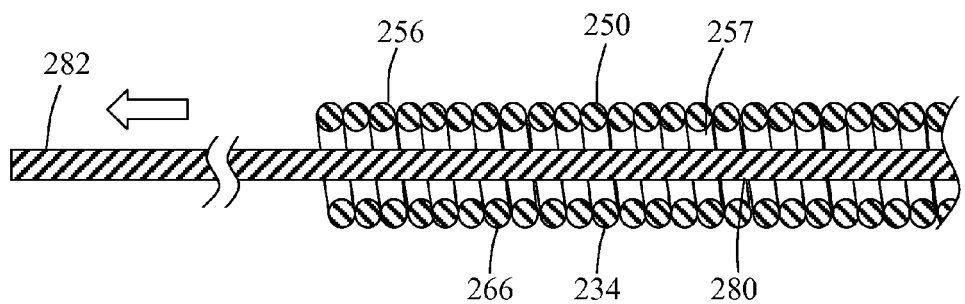
FIG. 12A is a partially sectioned view of the delivery system proximal end shown in FIG. 10A where the release wire is moved proximally relative to the delivery member.
Figure 12B:
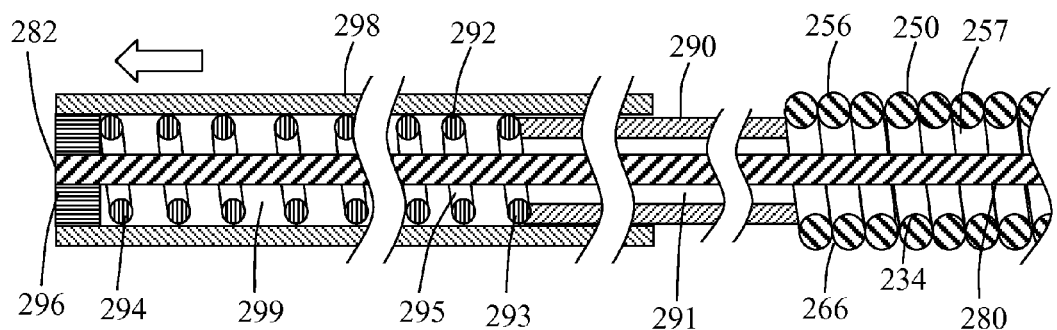
FIG. 12B is a partially sectioned view of the delivery system proximal end shown in FIG. 10C where the release wire is moved proximally relative to the delivery member.

To release embolic coil 240 from delivery system 230, release member 280 is placed in a second configuration by moving release member proximal end 282 proximally, as shown in FIGS. 12A and 12B. FIG. 12A depicts the first embodiment of proximal region 256 of delivery member 250, illustrated in FIG. 10A, where release member 280 is moved proximally relative to delivery member coil 266 by pulling or withdrawing proximal end 282 from delivery member lumen 257. FIG. 12B depicts the third embodiment of proximal region 256 of delivery member 250, illustrated in FIG. 10C, where release member 280 is moved proximally relative to delivery member coil 266 by stretching (elastically and or plastically) release member coil 292 (placing it in an extended configuration) to thereby causes release member proximal end 282 to move proximally relative to delivery member coil 266.

Due to the long length of delivery system 230, the force required to move release member 280 from its first configuration to its second configuration by proximally moving proximal end 282 relative to delivery member 250 is highly dependent upon the degree of tortuosity encountered by delivery system 230 and the amount of friction between components of the system. In order to minimize the amount of force required to be applied to proximal end 282 for release of embolic coil 240, it is preferable that release member 280 is coated with a lubricious surface. Preferably, release member 280 may be coated with a thin fluoropolymer such as PTFE or ETFE. Other hydrophobic or hydrophilic biocompatible polymers having a low coefficient of friction (such as Parylene) may also be suitable for coating the release member or the interior of the delivery member. Alternatively, lubricants such as silicone oils and submicron or nano-particles of tungsten disulfide, tantalum disulfide, molybdenum disulfide and boron nitride may be applied to the surfaces of components to reduce friction between the components and thusly reduce the required force necessary to move proximal end 282 proximally to release embolic coil 240.

Figure 13:
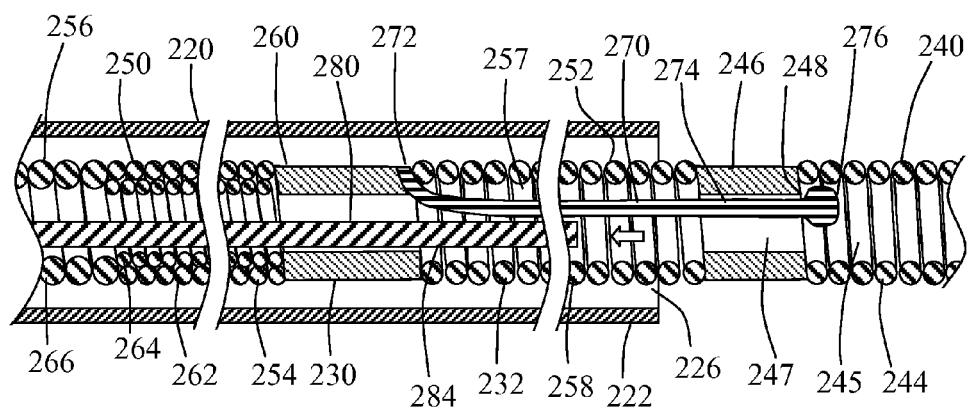
FIG. 13 is a partially sectioned view of the delivery system distal end engaged with the embolic coil where the release wire is moved proximally relative to the coil.
Figure 14:
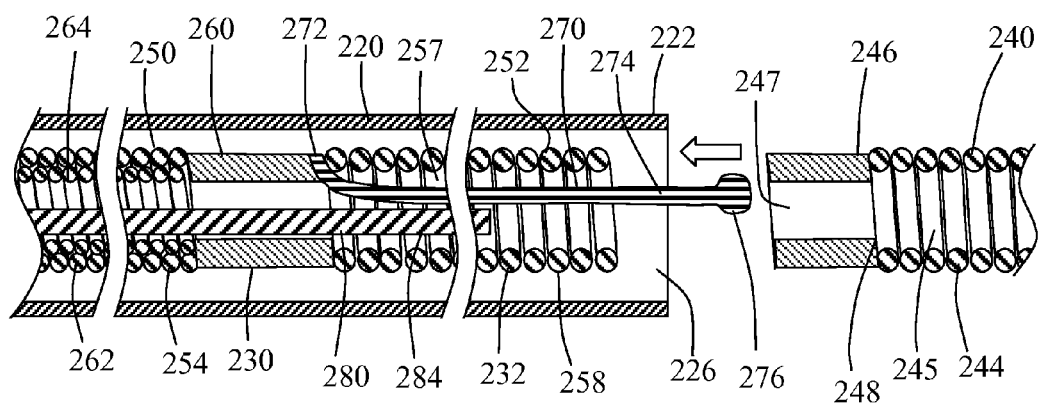
FIG. 14 is a partially sectioned view of the delivery system distal end moved proximally to release the embolic coil.

FIG. 13 illustrates the distal region 232 of deliver system 230 during the proximal movement of release member proximal end 282. As release member proximal end 282 is moved proximally relative to delivery member 250, release member 280 moves to its second configuration in which release member distal end 284 is withdrawn from coupling member aperture 247. In the second configuration of release member 280, distal end 284 does not cooperate with engagement member 270 to restrict engagement member distal end 274 from being withdrawn from coupling member 246. Additionally, in the second configuration tip member 276 is no longer restricted from moving proximally through aperture 247 although delivery member 250 may still be coupled to embolic coil 240. As shown in FIG. 14, delivery system 230 is moved proximally, along with engagement member 270, such that distal end 274 is removed from aperture 247 to thereby release embolic coil 240 at the target site.

During the treatment of delicate aneurysms (ruptured and unruptured), the positioning of the embolic coil prior to release is extremely important. Another critical aspect of aneurysm treatment is to insure that release of the embolic coil from the delivery system not cause substantial movement of the positioned embolic coil. FIGS. 13 & 14 illustrate the release of an implant according to an embodiment of deployment system 210 where distal region 252 of delivery member 250 takes the form of coil 258. Coil 258 is preferably formed from a resilient material making the coil flexible and potentially axially compressible in length, however, in this embodiment, coil 258 has a length which does not extend distal to distal end 274 of engagement member 270. As shown in FIG. 13, when release member 280 is moved to its second configuration, during the release of the embolic coil, tip member 276 does not substantially move its position relative to coupling member 246. This indicates that coil 258 although flexible and potentially axially compressible in length, does not supply a force to coupling member 246 that would cause tip member 276 to move its position relative to coupling member 246. As previously discussed, FIG. 14 illustrates the proximal movement of delivery system 230 such that engagement member distal end 274 is removed from coupling member 246 to release embolic coil 240 at the target site.

Figure 15:
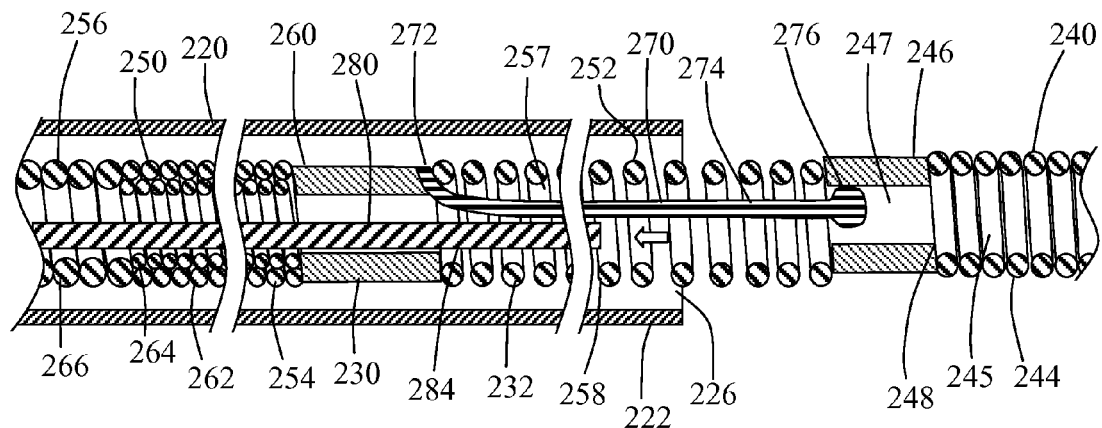
FIG. 15 is a partially sectioned view of the delivery system distal end engaged with the embolic coil where the release wire is moved proximally relative to the coil according to another embodiment of the present invention.
Figure 16A:
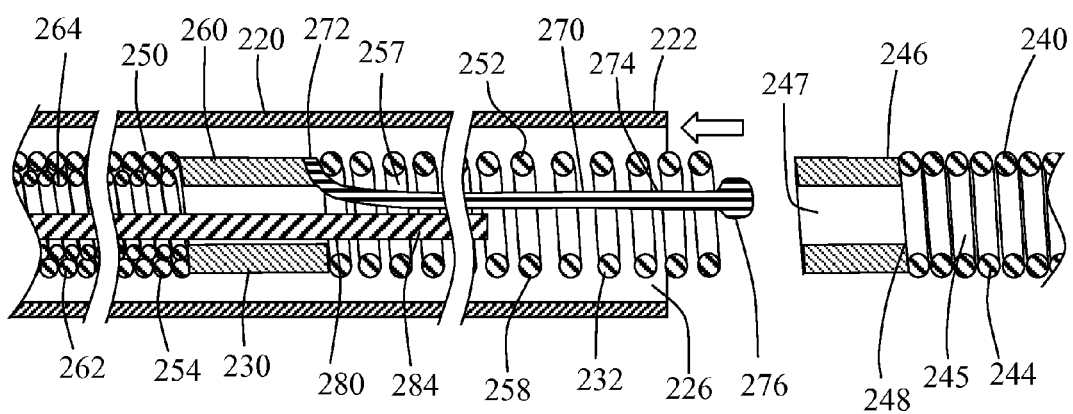
FIG. 16A is a partially sectioned view of the delivery system distal end moved proximally to release the embolic coil according to another embodiment of the present invention.
Figure 16B:
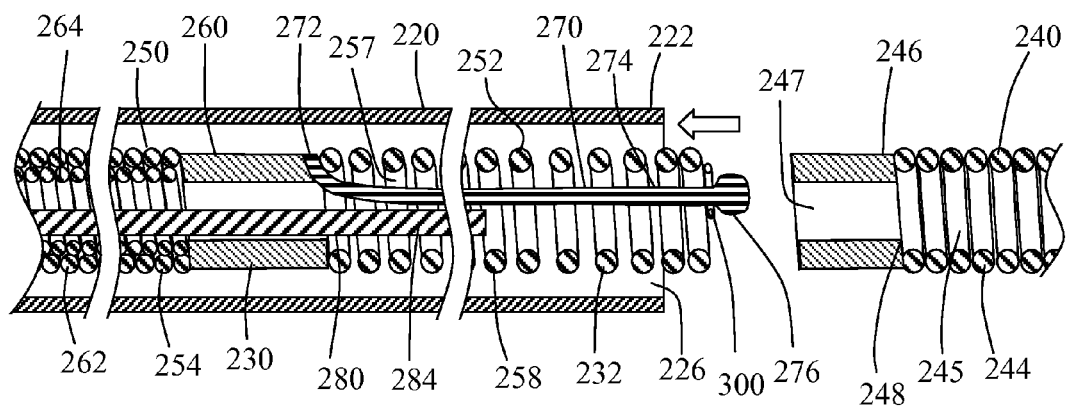
FIG. 16B is a partially sectioned view of the delivery system distal end moved proximally to release the embolic coil according to yet another embodiment of the present invention.
Figure 16C:
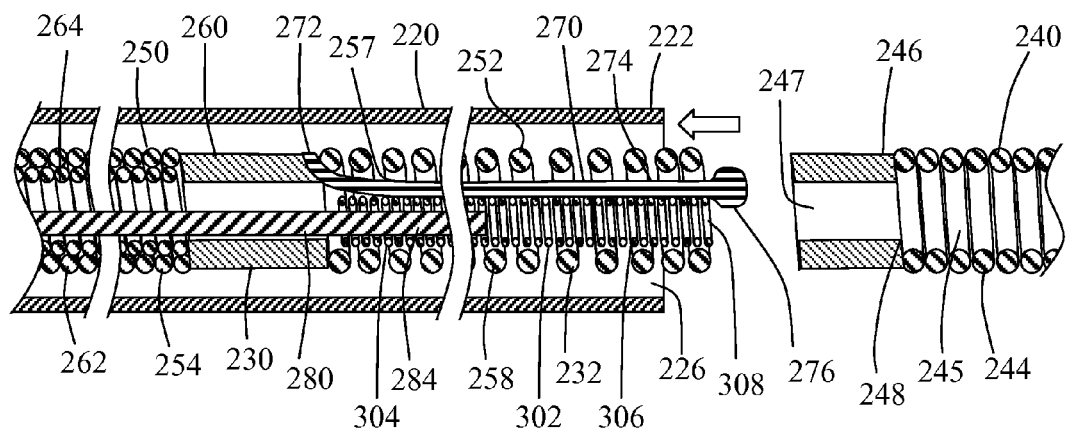
FIG. 16C is a partially sectioned view of the delivery system distal end moved proximally to release the embolic coil according to still yet another embodiment of the present invention.

While the aforementioned discussion indicates a desire to have no substantial movement of the embolic coil during release of the embolic coil, some movement to aid in the uncoupling may be desirable. FIGS. 15 & 16A illustrate the release of an implant according to another embodiment of deployment system 210 where distal region 252 of delivery member 250 takes the form of coil 258. In this embodiment, coil 258 does not extend distal to tip member 276 of engagement member 270, however coil 258 may apply a slight force to coupling member 246. As shown in FIG. 15, when release member 280 is moved to its second configuration, during the release of the embolic coil, tip member 276 is moved proximally relative to engagement portion 248 (more accurately, engagement portion 248 is moved distally relative to tip member 276) although delivery system 230 is still engaged with embolic coil 240. This small amount of movement ensures that when delivery system 230 is retracted to disengage embolic coil 240 as shown in FIG. 16A, tip member 276 is proximal to engagement portion 248 as not to provide a "catch" or resistance that could translate into undesired embolic coil movement. Controlling the length of coil 258 to apply a slight force to coupling member 246 while not extending distal to tip member 276 may be somewhat difficult. FIG. 16B illustrates an alternative delivery system 230 in which coil 258 includes a mechanical stop 300 fixedly secured at its distal end. Mechanical stop 300 preferably takes the form of a ring or washer having an aperture large enough to slidably accommodate engagement member 270 but not allow passage of tip member 276. The configuration of mechanical stop 300 allows coil 258 to apply a slight force to coupling member 246 to position tip member 276 proximal to engagement portion 248 once release member 280 is in its second configuration while insuring that coil 258 does not extend distal to tip member 276. FIG. 16C illustrates yet another alternative delivery system 230 in which coil 258 includes a mechanical stop 302 fixedly secured at its distal end. Mechanical stop 302 preferably takes the form of a coil having proximal end 304, distal end 306 and lumen 308 where lumen 308 is large enough to slidably accommodate release member distal end 284. The distance between the outer diameter of mechanical stop 302 and inner diameter of coil 258 accommodates engagement member 270 but does not allow the passage of tip member 276. The coil configuration of mechanical stop 302 allows coil 258 to apply a slight force to coupling member 246 to position tip member 276 proximal to engagement portion 248 once release member 280 is in its second configuration while insuring that coil 258 does not extend distal to tip member 276. Additionally mechanical stop 302 acts as a bearing thereby reducing the force exerted on release member distal end 284 by engagement member 270 when coil 258 is in a flexed configuration. This allows release member 280 to freely move when delivery system 230 placed in a tortuous anatomy.

Figure 17:
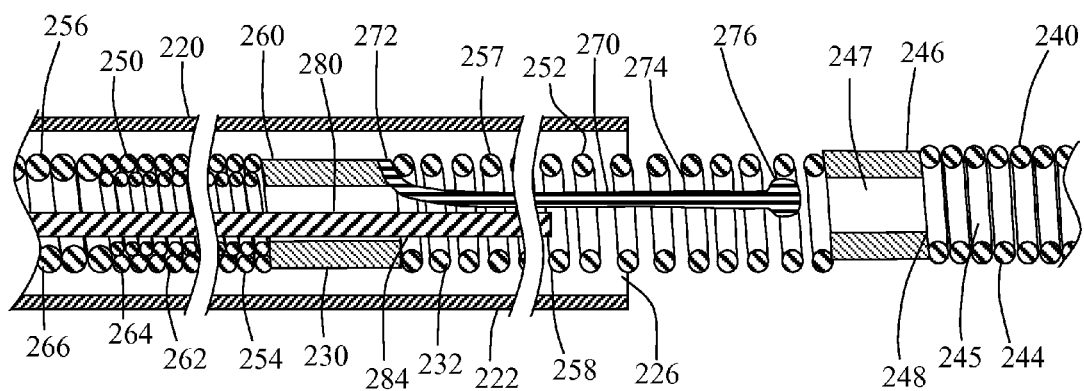
FIG. 17 is a partially sectioned view of the delivery system distal end engaged with the embolic coil where the release wire is moved proximally relative to the coil according to another embodiment of the present invention.
Figure 18:
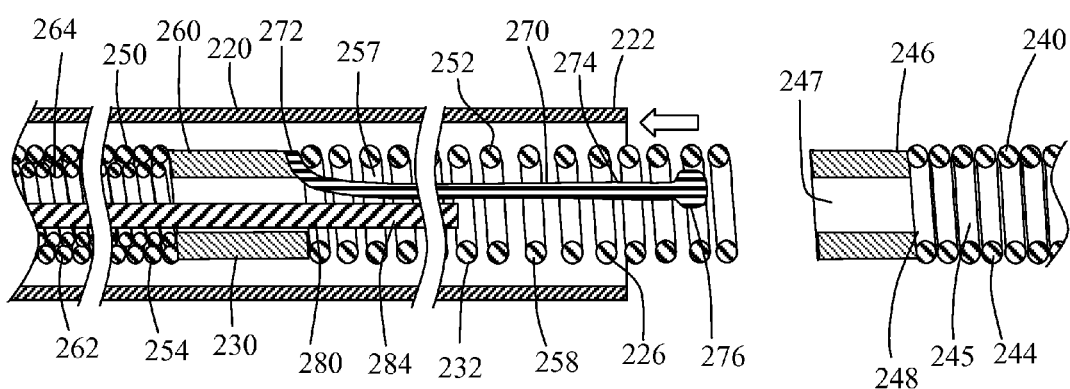
FIG. 18 is a partially sectioned view of the delivery system distal end moved proximally to release the embolic coil according to still yet another embodiment of the present invention.

For the placement of embolic coils or other implants where movement of the proximal end during release from the deployment system is less critical, there is provided yet another embodiment of deployment system 210 where distal region 252 of delivery member 250 takes the form of coil 258. In this embodiment, coil 258 extends distal to tip member 276 of engagement member 270 and coil 258 may apply a force to coupling member 246 to aid in the uncoupling of engagement member 270 from coupling member 276. As shown in FIG. 17, when release member 280 is moved to its second configuration, during the release of the embolic coil, coupling member 246 is moved distally relative to tip member 276 such that engagement member 270 is no longer in contact with coupling member 246 although coil 258 may still be in contact with embolic coil 240. FIG. 18 illustrates the proximal movement of delivery system 230, such that coil 258 of delivery member 250 separates from embolic coil 240.

Figure 19:
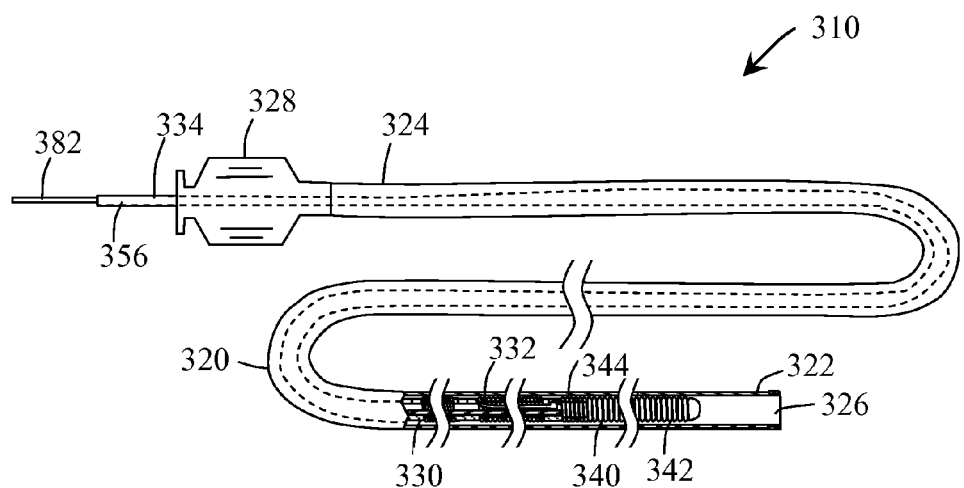
FIG. 19 is a partially sectioned view of an embolic coil deployment system according to yet another embodiment of the present invention.

FIG. 19 generally illustrates a medical implant deployment system 310 according to another embodiment of the present invention which includes delivery catheter 320 having a distal end 322, a proximal end 324, a lumen 326 extending therethrough and a catheter hub 328 affixed to proximal end 324, a delivery system 330 having a distal end 333 and a proximal end 334 and an embolic coil 340 having a distal end 342 and a proximal end 344 that is releasably coupled to the distal end 332 of delivery system 330. Embolic coil 340 is a medical implant of a general type suitable for use in occluding a vessel, lumen, duct or aneurysm.

Embolic coil 340 is generally formed from a primary coil of a helically wound wire 41, made from a material which is biocompatible and preferably radio-opaque. Suitable biocompatible materials include metals such as platinum, platinum alloys, stainless steel, nitinol, tantalum and gold and plastics such as nylons, polyesters, polyolefins and fluoropolymers. The wire usually has a circular cross-section, however, non-circular cross-sections, such as "D" shapes, are used in commercially available coils. The diameter of the wire may range from 0.0001" to about 0.010" and is largely dependent upon the particular clinical application for the coil. The diameter of the primary coil is generally dependent upon the wire diameter and the diameter of the mandrel used for winding. The primary coil diameter typically ranges from 0.002" to about 0.060" and is also dependent upon on the clinical application. The wound primary coil is typically removed from the mandrel leaving the coil with a lumen 345. In addition to the aforementioned method of winding a coil, there are other "mandrel-less" forming processes that are suitable for making primary coils that plastically deform the wire into coil. The formed primary coils may be further processed to have a secondary shape such as a helix, sphere, "flower", spiral or other complex curved structure suited for implantation in a particular anatomical location. The secondary shape is imparted to the coil through thermal and or mechanical means. Thermal means include forming the primary coil into a desired shape using a die or forming tool and then heat treating the coil to retain the secondary shape. Mechanical means include plastically deforming the primary coil into the desired shape or the use of a shaped resilient core wire inserted into the lumen of the primary coil to impart a shape to the coil. The length of the elongate primary coil ranges from 0.1 cm to about 150 cm with a preferred range of about 0.5 cm to about 70 cm. The distal end of the coil is typically rounded or beaded to make the coil end more atraumatic. Other variations of embolic coils suitable for use include stretch resistant coils, coils that incorporate a stretch resistant member(s) (within the coil lumen or exterior to the coil) that limit undesirable elongation of the primary coil during device manipulation and coated or modified coils that enhance occlusion through coils surface modifications, addition of therapeutics or volume filling materials (foams, hydrogels, etc.).

Figure 20:
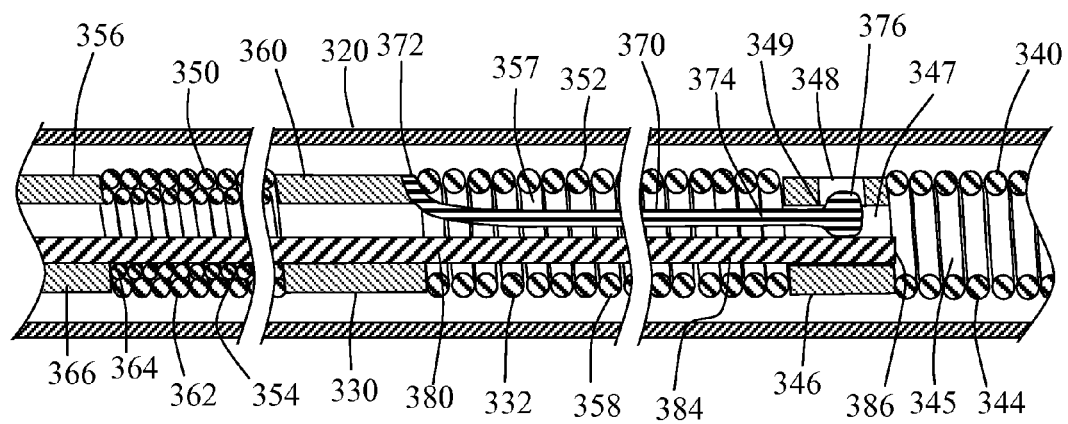
FIG. 20 is an enlarged partially sectioned view showing a distal portion of the embolic coil deployment system of FIG. 19.

FIG. 20 illustrates in more detail the construction of the implant deployment system 310 with the implant, coil 340, being positioned within lumen 326 of catheter 320. Embolic coil 340 includes a generally tubular headpiece coupling member 346 positioned at coil proximal end 344. Headpiece coupling member 346 includes a first aperture 347 extending longitudinally, a second aperture 348 extending through the tubular wall and an engagement portion 349. Delivery system 330 includes a tubular delivery member 350 having a distal region 352, an intermediate region 354, a proximal region 356 and a lumen 357 extending therethrough. Distal region 352 of delivery member 350 preferably takes the form of a helically wound coil 358 having a wire diameter ranging from 0.0005 in to 0.006 in and a preferred wire diameter range of about 0.001 in to 0.003 in. Distal region 352 has an axial length that ranges from about 1 cm to about 10 cm and preferably ranges from about 2.5 cm to about 3.5 cm. Tubular marker band 360 is coupled to the proximal portion of coil 358. Intermediate region 354 of delivery member 350 preferably takes the form of a multi-filar wound coil having an outer coil 362 having a number of filaments ranging from 5 to 12 and with filament diameters ranging from 0.001 in to 0.005 in and a preferred number of filaments ranging from 6 to 8 and preferred filament diameters between about 0.0015 in and 0.0035 in and an inner coil 364 having a number of filaments ranging from 5 to 12 and with filament diameters ranging from 0.001 in to 0.005 in and a preferred number of filaments ranging from 6 to 8 and preferred filament diameters between about 0.0015 in and 0.0035 in. Intermediate region 354 has an axial length that ranges from about 20 cm to about 50 cm and preferably ranges from about 30 cm to about 40 cm. The distal ends of intermediate region coils 362 and 364 are preferably welded to the proximal end of marker band 360. Proximal region 356 of delivery member 350 preferably takes the form of a hypotube having a wall 366. Proximal region 356 has an axial length that ranges from about 120 cm to about 170 cm and preferably ranges from about 140 cm to about 160 cm. The distal end of wall 366 is preferably welded to the proximal end of intermediate region 354. While the aforementioned distal, intermediate, proximal regions of delivery member 350 are presented with their respective preferred forms to produce a delivery member having a small diameter profile, these regions of delivery member 350 may also take the form of components used in the construction of catheters and microcatheters, that include laser cut hypotubes, standard hypotubes, braided materials, tubular polymer materials and composites.

Delivery system 330 also includes an engagement member 370 having a proximal end 372, a distal end 374 and a tip member 376 coupled to distal end 374. Tip member 376 preferably takes the form of a generally spherical bead, however, shapes such as rounded disks and other curvilinear geometries that allow the tip member to easily disengage from the engagement portion of the implant coupling member may also be suitable. Engagement member 370 is shown positioned at the distal region 352 of delivery member 350 and secured to delivery member 350 preferably by laser welding but may take the form of any suitable joining technique such as soldering, spot welding, adhesives and ultrasonic welding. Delivery system 330 also includes an elongate release member 380 having a proximal end 382, a distal end 384 and a tip portion 386. Release member 380 preferably takes the form of an elongate resilient nitinol wire although other materials such as stainless steel, platinum alloys, glass or ceramic fibers, polymeric fibers, etc. and forms such as tubes or cables may be suitable. Release member 380 typically has a length which is longer than the combined lengths of the distal, intermediate and proximal regions of delivery system 330. Release member 380 is positioned within lumen 357 of delivery member 350 where the proximal end 382 extends proximal to proximal region 356.

As previously discussed, the proximal end 344 of embolic coil 340 is releasably coupled to the distal end 332 of delivery system 330. More particularly, delivery member distal region 352 and engagement member 370 engage coupling member 346 positioned at coil proximal end 344. As shown in FIG. 20, the distal end 374 of engagement member 370 is positioned within aperture 347 of coupling member 346. Aperture 347 has a diameter larger than the diameter of tip member 376, thereby allowing tip member 376 to be easily inserted into or removed from coupling member 346. In a first configuration, distal end 384 of release member 380 is positioned within aperture 347 of coupling member 346 adjacent to engagement member distal end 374, while tip member 376, is partially positioned within aperture 348 and is engaged with engagement portion 349. The diameters of release member distal end 384 and engagement member distal end 374 cooperatively restrict tip member 376 from being withdrawn through aperture 347. While in this first configuration, coil proximal end 344 is securely coupled to delivery member distal region 352 and allows delivery member 350 to advance or retract embolic coil 340 within the catheter. In a second configuration, distal end 384 of release member 380 is withdrawn from aperture 347 of coupling member 346 allowing tip member 376 of engagement member distal end 374 to be removed from aperture 348 and disengage from engagement portion 349. The removal of release member distal end 384 from aperture 347 allows tip member tip member 376 to be withdrawn from aperture 347 thereby uncoupling coil 340 from the delivery member.

Figure 21:
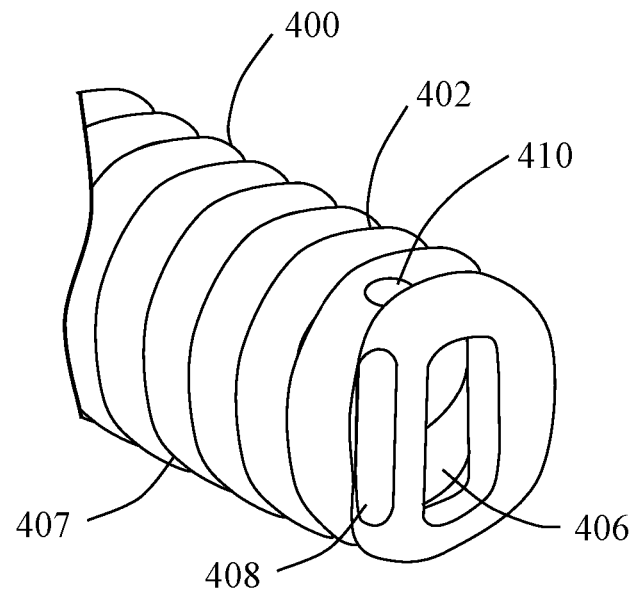
FIG. 21 is a perspective view of a coil component of the delivery system distal end according to an embodiment of the present invention.

FIG. 21 illustrates distal region 400, which is a delivery member component having an alternative construction to previously disclosed distal regions, for use with any of the aforementioned delivery members. Distal region 400 takes the form of a helically wound coil having a distal end 402, a proximal end 404 (not shown) and a lumen 406 extending there between wound from wire 407. Typically wire 407 is round and has a diameter that ranges from about 0.0005 in to 0.006 in and a preferred range of about 0.001 in to 0.003 in. Alternatively the shape of the wire may be rectangular or round wire which has been flattened and has a thickness which is smaller than the for example 0.0075 in by 0.004". Distal region 400 has an axial length that ranges from about 1 cm to about 10 cm and preferably ranges from about 2.5 cm to about 3.5 cm. Located at distal end 402, distal region 400 includes end loop 408, which has been formed such that the loop and the lumen with in the loop has a generally rectangular shape. To maintain this shape and to keep the wire from unraveling, end loop 408 may be secured at weld 410 to the adjacent by loop. The rectangular lumen shape typically has a width that accommodates either the diameter of the release member or the engagement member and a height that accommodates the diameter of both the release member and the engagement when they are side by side while restricting the engagement member tip member from entering the lumen.

Figure 22:
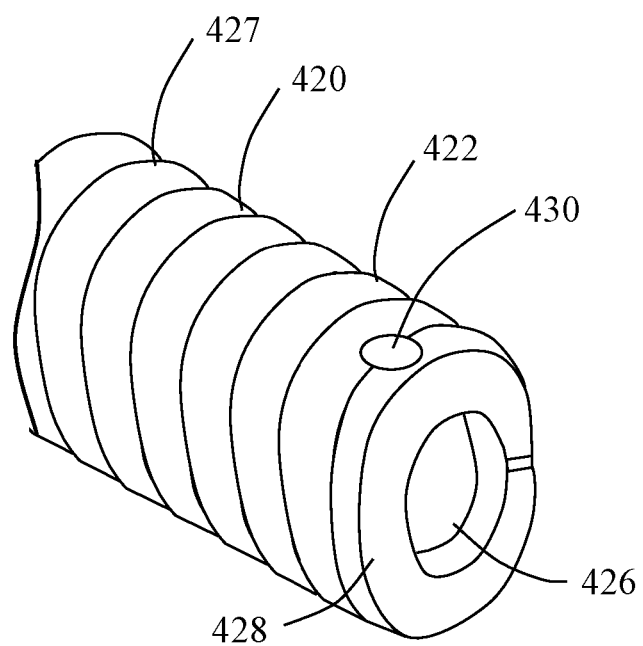
FIG. 22 is a perspective view of an alternative coil component of the delivery system distal end according to still another embodiment of the present invention.

FIG. 22 illustrates distal region 420, which is a delivery member component having an alternative construction to previously disclosed distal regions, for use with any of the aforementioned delivery members. Distal region 420 takes the form of a helically wound ellipse shaped coil, having a distal end 422, a proximal end 424 (not shown) and an ellipse shaped lumen 426 extending there between wound from wire 427. Typically wire 427 is round and has a diameter that ranges from about 0.0005 in to 0.006 in and a preferred range of about 0.001 in to 0.003 in. Alternatively the shape of the wire may be rectangular or round wire which has been flattened and has a thickness which is smaller than the for example 0.0075 in by 0.004". Distal region 420 has an axial length that ranges from about 1 cm to about 10 cm and preferably ranges from about 2.5 cm to about 3.5 cm. Located at distal end 422, distal region 420 includes end loop 428. To keep the wire from unraveling, end loop 428 may be secured at weld 430 to the adjacent by loop. The ellipse lumen shape typically has a width that accommodates either the diameter of the release member or the engagement member and a height that accommodates the diameter of both the release member and the engagement when they are side by side while restricting the engagement member tip member from entering the lumen.

Figure 23A:
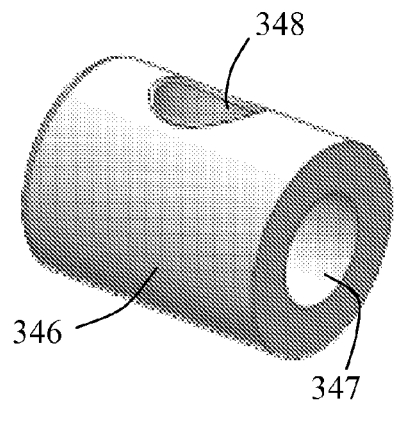
FIGS. 23A and 23B are perspective and side views of a coupling member of the present invention.
Figure 23B:
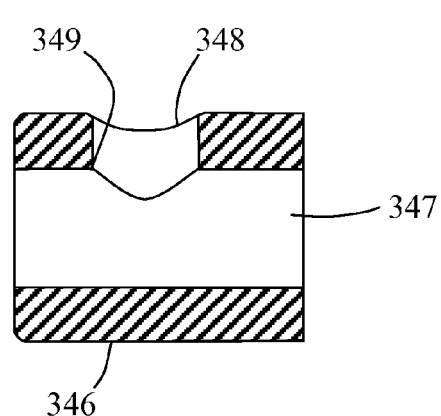
Figure 24A:
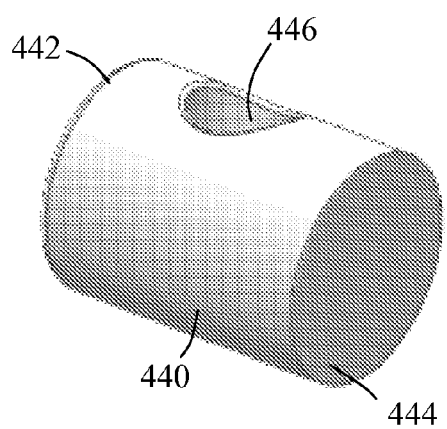
FIGS. 24A and 24B are perspective and side views of an alternative coupling member according to another embodiment of the present invention.
Figure 24B:
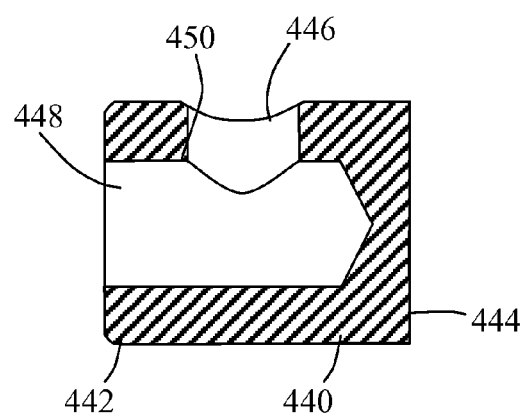
Figure 25:
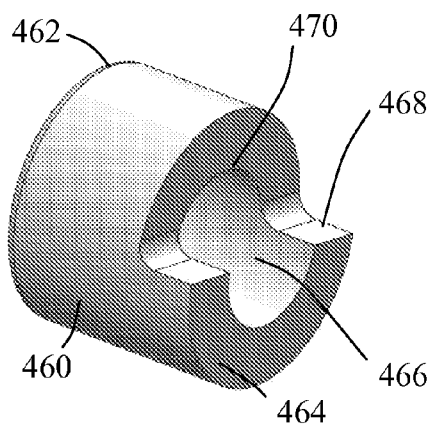
FIG. 25 is perspective view of an alternative coupling member according to still another embodiment of the present invention.
Figure 26A:
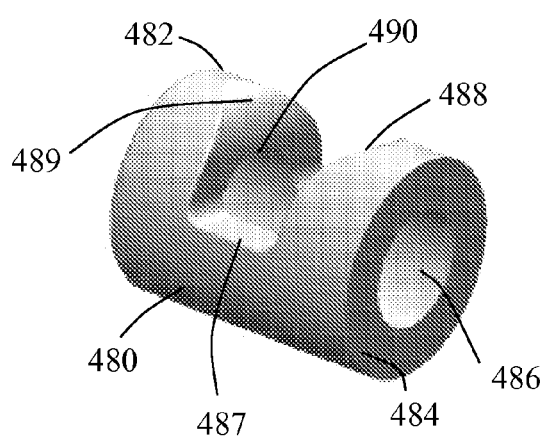
FIGS. 26A through 26C are perspective and side views of an alternative coupling member according to still yet another embodiment of the present invention.
Figure 26B:
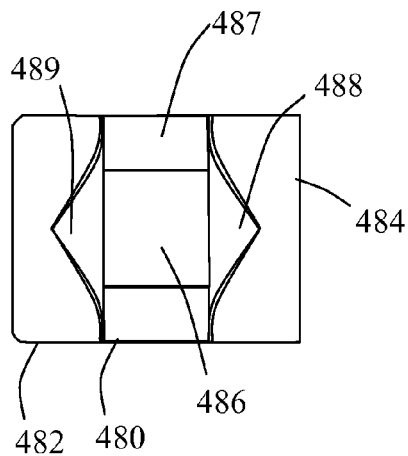
Figure 26C:
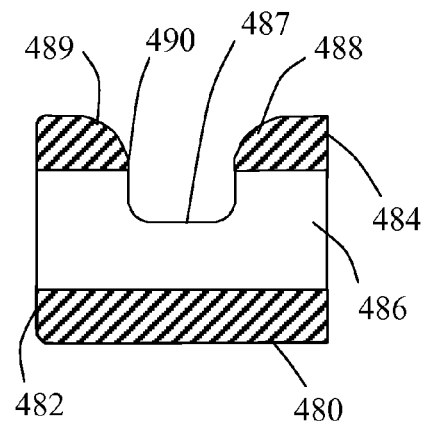
Figure 27A:
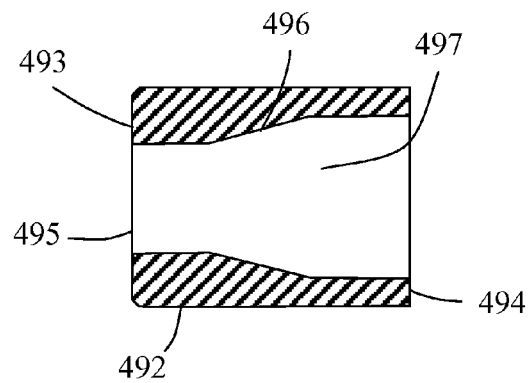
FIG. 27A is a sectional view of an alternative coupling member according to another embodiment of the present invention.
Figure 27B:
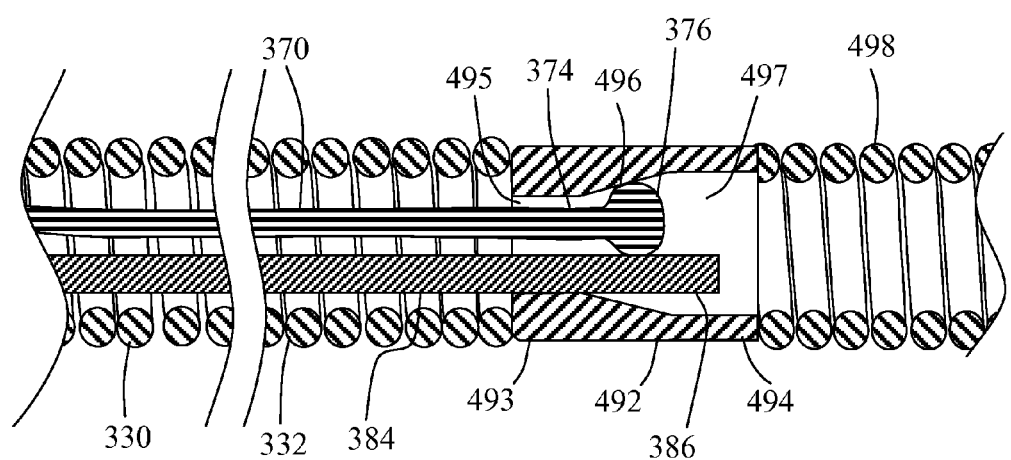
FIG. 27B is a sectional view of the coupling member in FIG. 27A coupled to an implant and the distal portion of a delivery system according to an embodiment of the present invention.

FIGS. 23A through 27B illustrate various configurations and views of alternate coupling members that may be fixedly attached to a medical implant, such as an embolic coil, stent, filter or vascular occlusion device, and removably attached to a delivery member for delivery to a target site within the body. All of the coupling members are typically formed of a biocompatible material suitable for implantation, such as platinum, iridium, gold, tantalum, stainless steel and other alloys including cobalt-chromium, and are preferably radio-opaque as to be visible under fluoroscopy. FIG. 23A shows tubular coupling member 346 prior to fixedly attaching it to proximal end 344 of embolic coil 340. Coupling member 346 includes a through lumen 347 and a side aperture 348 through the tubular wall. Shown in FIG. 23B, engagement portion 349, which is formed as part of the wall of the aperture 348 is generally the position at which the tip member of an engagement member, extending from a delivery system, is positioned within lumen 347 and engages the coupling member. FIG. 24 A depicts alternate coupling member 440 having a first end 442 a second end 444 a side aperture 446 and an interior cavity 448. Typically, coupling member 440 is formed from a solid rod in which cavity 448 is drilled or machined from first end 442, leaving second end 444 closed. Second end 444 is typically the portion of coupling member 440 that would be fixedly attached to an implant device. Shown in FIG. 24B, engagement portion 450, which is formed as part of the wall of the aperture 446 is generally the position at which the tip member of an engagement member, extending from a delivery system, is positioned within cavity 448 and engages the coupling member. FIG. 25 shows coupling member 460 which is another component variant. Coupling member 460 is generally tubular and has a first end 462, a second end 464 and a lumen 466 extending there between. A portion of the tubular wall is removed at second end 464 forming slot 468. Slot 468 is typically formed by machining, cutting or grinding away a portion of the tubular wall leaving coupling member 460 with an "L" shaped configuration. Second end 464 is typically the portion of coupling member 460 that would be fixedly attached to an implant device. Engagement portion 470, which is formed as part of the wall left by slot 468 is generally the position at which the tip member of an engagement member, extending from a delivery system, is positioned within lumen 466 and engages the coupling member. FIGS. 26A through 26C illustrates yet another coupling member 480 having some similarity to coupling member 460. Coupling member 480 is generally tubular and has a first end 482, a second end 484 and a lumen 486 extending there between. A portion of the tubular wall is removed between first end 482 and second end 484 forming a slot 487. Slot 487 is typically formed by machining, cutting or grinding away a portion of the tubular wall leaving coupling member 480 with a "U" shaped configuration. The outer edges 488 and 489 are typically rounded to remove any sharp edges. Second end 484 is typically the portion of coupling member 480 that would be fixedly attached to an implant device. Engagement portion 490, which is formed as part of the wall left by slot 487 is generally the position at which the tip member of an engagement member, extending from a delivery system, is positioned within lumen 486 and engages the coupling member. The coupling members represented in FIGS. 23 through 26C illustrate couplers that when coupled to a delivery system as described, do not allow the coupling member to freely rotate about the longitudinal axis when engaged. When a delivery system coupled to these coupling members is torqued, a torsional force is also applied to the coupling member and depending on how the coupling member is attached to the implant, that torsional force may be transmitted to the implant. When properly designed this may be a desirable feature, affording some benefits when rotationally orienting the implant. FIG. 27A illustrates still yet another coupling member 492 having some similarities to previously described coupling members. Coupling member 492 is generally cylindrical and tubular and includes a first end 493, a second end 494, an aperture 495 and an engagement portion 496. Aperture 495 begins at first end 493 having a first diameter and extends axially within coupling member 492 towards second end 494 forming lumen 497. At an axial location between first and second ends 493 and 494 respectively the diameter of lumen 497 increases in a tapered or flared manner such that the diameter adjacent second end 494 is typically larger than the first diameter adjacent first end 493. Engagement portion 496 resides on the internal tapered wall of coupling member 492 and is positioned between first end 493 and second end 494. Engagement portion 496, which takes the form of the tapered portion of the coupling member internal wall is generally the position at which the tip member of an engagement member, extending from a delivery system, is positioned within lumen 497 and engages the coupling member. While having some similarities to the previously described coupling members in FIGS. 23 through 26C, coupling member 492 does not allow the transmission of torsional force to an implant from a coupled delivery system which has been torqued. The design of coupling member 492 allows the coupling member to rotate about the longitudinal axis of a delivery system when coupled. As shown in FIG. 27B, coupling member 492 is fixedly attached to an implant device, such as embolic coil 498 at second end 494 and releasably coupled to delivery system 330 at first end 493. The distal end 374 of engagement member 370 extends through aperture 495 and into lumen 497 concurrent with the distal end 384 of release member 380 being positioned within lumen 497 through aperture 495 to cooperatively cause tip member 376 of engagement member 370 to engage with engagement portion 496 thereby restricting the uncoupling of coupling member 492 from delivery system 330.

Figure 28:
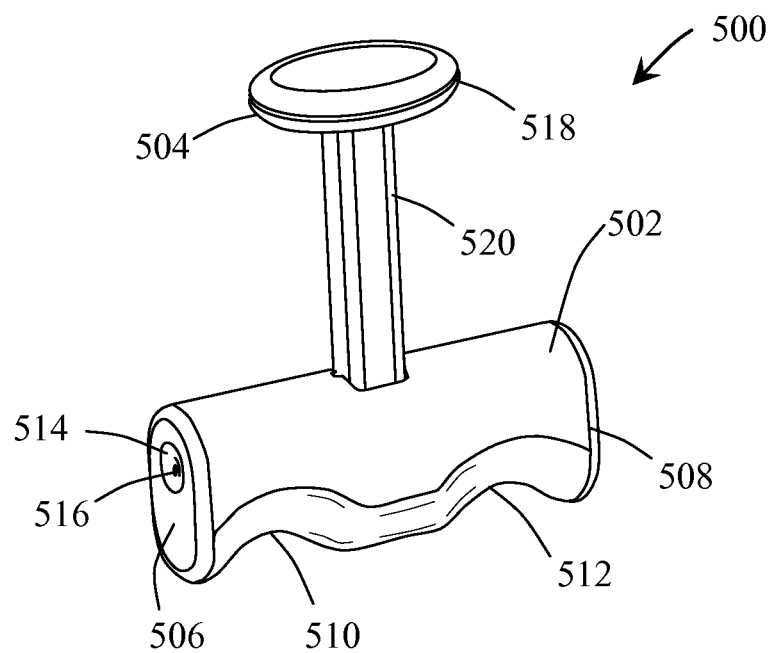
FIG. 28 is a perspective view of a handle assembly suitable for attachment to the proximal region of the delivery member according to an embodiment of the present invention.
Figure 29:
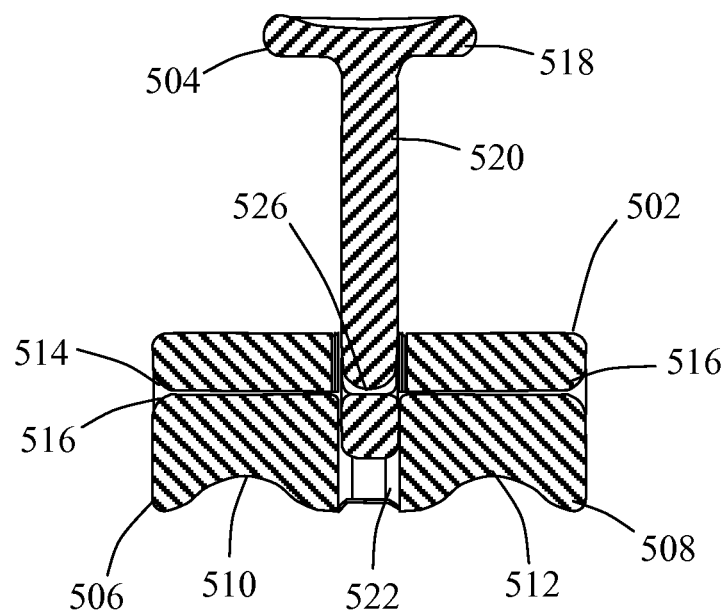
FIG. 29 is a partial sectional view of the handle assembly of FIG. 28.

The release of a medical implant from a deployment or delivery system as previously described, requires moving the release member from its first configuration in which the release member and an engagement member cooperatively engage the implant coupling member, to its second configuration in which the release member removes the cooperative engagement with the implant coupling member. Typically this is accomplished by moving the release member proximally relative to the delivery member thereby removing the distal end of the release member from the implant coupling member. FIGS. 28 and 29 illustrate a light weight removable handle assembly 500 that can quickly facilitate releasing the implant at a target site. Handle assembly 500 includes a housing body 502 and plunger member 504. Housing body 502 has first and second ends 506 and 508 and first and second contour portions 510 and 512 respectively. First end 506 includes a recessed taper 514 and a housing lumen 516 that extends from first end 506 to second end 508. Plunger member 504 includes a top portion 518 connected to an elongate shaft 520. Housing body 502 includes a shaft channel 522 positioned between the first and second ends and generally intersects housing lumen 516 perpendicularly. Elongate shaft 520 further includes a centering tab 524 and a transverse lumen 526 that extend perpendicular to the long axis of shaft 520. Handle assembly 500 has a first configuration in which plunger shaft 520 is positioned within shaft channel 522 such that transverse lumen 526 of the plunger is collinearly aligned with housing lumen 516. Centering tab 524 mates with housing body 502 to preferentially place handle assembly 500 in said first configuration. Handle assembly 500 also has a second configuration in which plunger shaft 520 has been moved relative to the first configuration such that the shaft transverse lumen 526 is no longer collinearly aligned with housing lumen 516.

Figure 30:
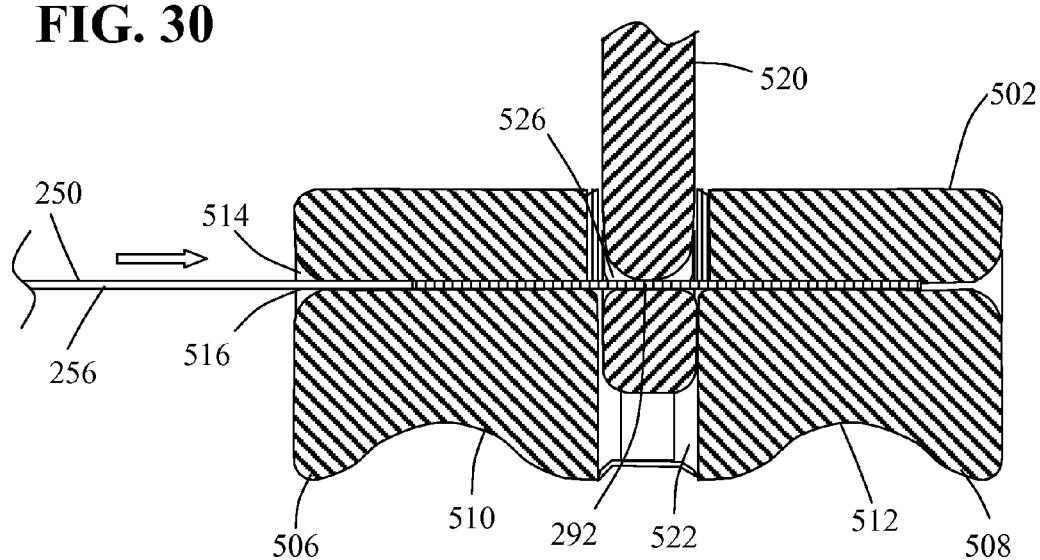
FIG. 30 is a partial sectional view of the handle assembly of FIG. 28 with the proximal region of the delivery member positioned within handle assembly lumen.
Figure 31:
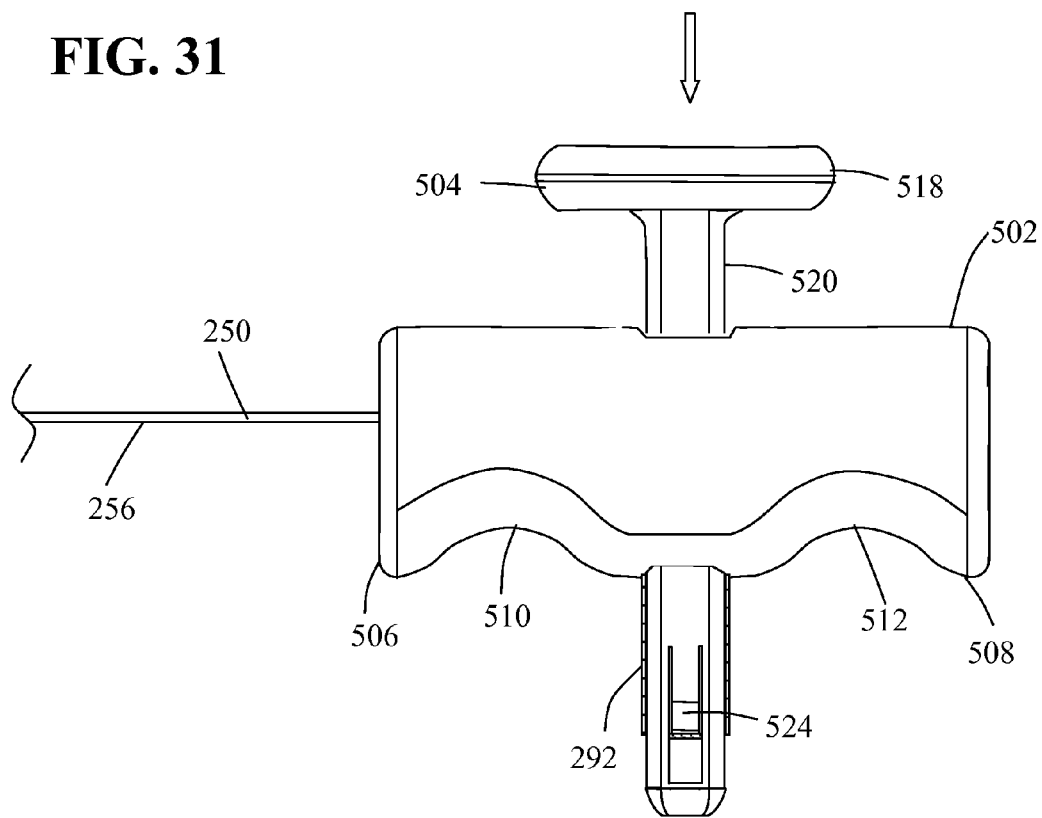
FIGS. 31 & 32 are side and partial sectional views of the handle assembly when operated thereby stretching the release coil member and moving the release member from its first configuration to its second configuration.
Figure 32:
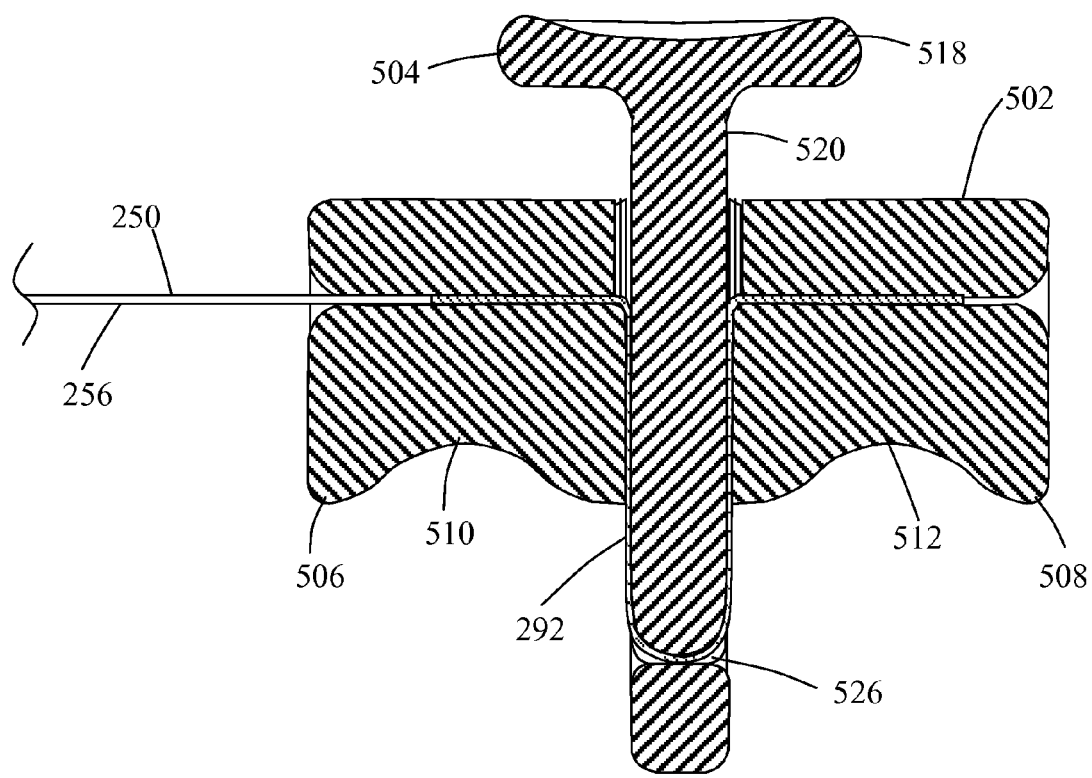

FIGS. 30 through 32 illustrate the operation of handle assembly 500 to release a medical implant coupled to a delivery system. Handle assembly 500 is placed in its first configuration and proximal region 256 of delivery member 250 is inserted into housing body 502. More specifically, proximal spring member 292, which is coaxially disposed about release member 280, is inserted into housing lumen 516 at first end 506 such that it extends through transverse lumen 526 of plunger shaft 520 and into housing lumen 516 towards housing second end 508, as shown in FIG. 30. Plunger member 504 of the handle assembly is then depressed and moved within housing channel 522 relative to the housing body 502, depicted in FIGS. 31 and 32, to displace transverse lumen 526 relative to housing lumen 516, thereby stretching proximal spring member 292 and moving release member 280 proximally relative to delivery member 250. As handle assembly 500 is placed in its second configuration, release member 280 is simultaneously placed in its second configuration thereby releasing the implant at the target site.

Numerous modifications exist that would be apparent to those having ordinary skill in the art to which this invention relates and are intended to be within the scope of the claims which follow.

That which is claimed is:

1. A medical implant deployment system for use in placing an implant at a preselected site within a vessel or lumen comprising:
  a flexible catheter having proximal and distal ends and a lumen extending therethrough,
  an elongated flexible delivery member having proximal and distal regions and a lumen extending therethrough, said delivery member being positioned within the lumen of said catheter,
  a medical implant having proximal and distal ends and a coupling member positioned at said implant proximal end, said coupling member including an engagement portion and an aperture disposed through said engagement portion, said implant being positioned within the lumen of said catheter and said implant being releasably coupled to said delivery member, a delivery member distal assembly positioned at the distal region of said delivery member including a tubular housing member having proximal and distal regions, proximal and distal ends and a lumen extending therethrough, wherein the proximal end of said tubular housing member is fixedly coupled to said delivery member, a resilient engagement member having proximal and distal ends and a tip member positioned at said engagement member distal end wherein the distal end of said engagement member extends distal to the distal region of said tubular housing member and is positioned within said coupling member aperture, and said tip member engages said engagement portion of said coupling member, wherein said distal end of said tubular housing member of said delivery member and said proximal end of said coupling member of said medical implant are positioned in an end-to-end abutting relationship, and an elongate release member having proximal and distal ends and being positioned within the lumen of said delivery member, said release member having a first configuration wherein the distal end of said release member is positioned within said coupling member aperture adjacent said engagement member and in cooperation with said engagement member restricts the uncoupling of said coupling member from said engagement member and a second configuration wherein the distal end of said release member allows the uncoupling of said coupling member from said engagement member, said release member being in said first configuration and being operable between said first and second configurations.

2. A medical implant deployment system according to claim 1 wherein the aperture of said coupling member is oriented parallel to the longitudinal axis of said delivery member.

3. A medical implant deployment system according to claim 1 wherein said implant is an occlusion device.

4. A medical implant deployment system according to claim 1 wherein said release member distal end is positioned proximal to said tip member in said first configuration.

5. A medical implant deployment system according to claim 1 wherein said release member distal end is positioned distal to said tip member in said first configuration.

6. A medical implant deployment system according to claim 1 wherein said release member distal end includes a taper.

7. A medical implant deployment system according to claim 1 wherein said release member proximal end includes a resilient spring member having proximal and distal ends wherein said spring member proximal end is coupled to said release member proximal end and the distal end of said spring member is coupled to the proximal region of said delivery member.

8. A medical implant deployment system according to claim 7 wherein said spring member has a first configuration that applies a force directed distally to the proximal end of said release member and a second configuration that applies a force directed proximally on the proximal end of said release member, said spring member being movable from said first configuration to said second configuration by moving said spring member proximally relative to said delivery member.

9. A medical implant deployment system according to claim 1 wherein said tubular housing member has a first length when said release member is in said first configuration and said tip member engages said engagement portion of said coupling member such that said housing member distal region is positioned proximal to said tip member and a second length when said release member is in said second configuration wherein said second length is greater than said first length.

10. A medical implant deployment system according to claim 9 wherein said tubular housing member distal region does not extend distal to said tip member of said engagement member when said release member is in said second configuration.

11. A medical implant deployment system according to claim 9 wherein said tubular housing member distal region extends distal to said tip member of said engagement member when said release member is in said second configuration.

12. An embolic coil delivery device for use in placing a coil at a preselected site within a vessel or lumen comprising:

an elongated flexible tubular delivery member having proximal, intermediate and distal regions, a delivery assembly coupled to the distal region of said delivery member including a tubular housing member having proximal and distal regions and a lumen extending therethrough, a resilient engagement member having proximal and distal ends and a tip member fixedly coupled to said engagement member distal end, wherein the proximal end is fixedly coupled to said delivery member and the distal end of said engagement member extends distal to the distal region of said tubular housing member, an elongate embolic coil having proximal and distal ends and a coupling member positioned at said coil proximal end, said coupling member including an engagement portion and an aperture disposed through said engagement portion, said embolic coil being positioned distal to and releasably coupled to said delivery assembly wherein the distal end of said engagement member is positioned within said coupling member aperture and said tip member engages said engagement portion, wherein said distal end of said tubular housing member of said delivery member and said proximal end of said coupling member of said embolic coil are positioned in an end-to-end abutting relationship, and a release member coupled to said delivery member having proximal and distal ends wherein the proximal end of said release member is positioned adjacent the proximal region of said delivery member and the distal end of said release member is positioned adjacent said delivery assembly distal region, said release member having a first configuration wherein the distal end of said release member is positioned within said coupling member aperture adjacent said engagement member and in cooperation with said engagement member restricts the uncoupling of said coupling member from said engagement member and a second configuration wherein the distal end of said release member allows the uncoupling of said coupling member from said engagement member, said release member being in said first configuration and being operable between said first and second configurations.

13. An embolic coil delivery device according to claim 12 wherein the aperture of said coupling member is oriented parallel to the longitudinal axis of said delivery member.

14. An embolic coil delivery device according to claim 12 wherein said embolic coil includes a stretch resistant member.

15. An embolic coil delivery device according to claim 12 wherein said release member distal end is positioned proximal to said tip member in said first configuration.

16. An embolic coil delivery device according to claim 12 wherein said release member distal end is positioned distal to said tip member in said first configuration.

17. An embolic coil delivery device according to claim 12 wherein said release member distal end includes a taper.

18. An embolic coil delivery device according to claim 12 wherein said release member proximal end includes a resilient spring member having proximal and distal ends wherein said spring member proximal end is coupled to said release member proximal end and the distal end of said spring member is coupled to the proximal region of said delivery member.

19. An embolic coil delivery device according to claim 18 wherein said spring member has a first configuration that applies a force directed distally to the proximal end of said release member and a second configuration that applies a force directed proximally on the proximal end of said release member, said spring member being movable from said first configuration to said second configuration by moving said spring member proximally relative to said delivery member.

20. An embolic coil deployment system for use in placing a coil at a preselected site within a vessel or lumen comprising:
    a flexible catheter having proximal and distal ends and a lumen extending therethrough,
    an elongated flexible delivery member having proximal and distal regions and a lumen extending therethrough, said delivery member being positioned within the lumen of said catheter,
    an embolic coil having proximal and distal ends and a coupling member positioned at said coil proximal end, said coupling member including an engagement portion and an aperture disposed through said engagement portion, said coil being positioned within the lumen of said catheter and said coil being releasably coupled to said delivery member,
    a delivery member distal assembly positioned at the distal region of said delivery member including a tubular housing member having proximal and distal regions, proximal and distal ends and a lumen extending therethrough, wherein the proximal end of said tubular housing member is fixedly coupled to said delivery member, a resilient engagement member having proximal and distal ends and a tip member positioned at said engagement member distal end wherein the distal end of said engagement member extends distal to the distal region of said tubular housing member and is positioned within said coupling member aperture, and said tip member engages said engagement portion of said coupling member,
    wherein said distal end of said tubular housing member of said delivery member and said proximal end of said coupling member of said embolic coil are positioned in an end-to-end abutting relationship, and
    an elongate release member having proximal and distal ends and being positioned within the lumen of said delivery member, said release member having a first configuration wherein the distal end of said release member is positioned within said coupling member aperture adjacent said engagement member and in cooperation with said engagement member restricts the uncoupling of said coupling member from said engagement member and a second configuration wherein the distal end of said release member allows the uncoupling of said coupling member from said engagement member, said release member being in said first configuration and being operable between said first and second configurations.

21. An embolic coil deployment system according to claim 20 wherein the aperture of said coupling member is oriented parallel to the longitudinal axis of said delivery member.

22. An embolic coil deployment system according to claim 20 wherein said embolic coil includes a stretch resistant member.

23. An embolic coil deployment system according to claim 20 wherein said release member distal end is positioned proximal to said tip member in said first configuration.

24. An embolic coil deployment system according to claim 20 wherein said release member distal end is positioned distal to said tip member in said first configuration.

25. An embolic coil deployment system according to claim 20 wherein said release member distal end includes a taper.

26. An embolic coil deployment system according to claim 20 wherein said release member proximal end includes a resilient spring member having proximal and distal ends wherein said spring member proximal end is coupled to said release member proximal end and the distal end of said spring member is coupled to the proximal region of said delivery member.

27. An embolic coil deployment system according to claim 26 wherein said spring member has a first configuration that applies a force directed distally to the proximal end of said release member and a second configuration that applies a force directed proximally on the proximal end of said release member, said spring member being movable from said first configuration to said second configuration by moving said spring member proximally relative to said delivery member.

28. An embolic coil deployment system according to claim 20 wherein said tubular housing member has a first length when said release member is in said first configuration and said tip member engages said engagement portion of said coupling member such that said housing member distal region is positioned proximal to said tip member and a second length when said release member is in said second configuration wherein said second length is greater than said first length.

29. An embolic coil deployment system according to claim 28 wherein said tubular housing member distal region does not extend distal to said tip member of said engagement member when said release member is in said second configuration.

30. An embolic coil deployment system according to claim 28 wherein said tubular housing member distal region extends distal to said tip member of said engagement member when said release member is in said second configuration.

31. A medical implant deployment system for use in placing an implant at a preselected site within a vessel or lumen comprising:
    a flexible catheter having proximal and distal ends and a lumen extending therethrough, an elongated flexible delivery member having proximal and distal regions and a lumen extending therethrough, said delivery member being positioned within the lumen of said catheter, an implant having proximal and distal ends and a coupling member fixedly positioned at said implant proximal end, said coupling member including an aperture and an engagement portion, said implant being positioned within the lumen of said catheter and said implant being releasably coupled to said delivery member, a delivery member distal assembly positioned at the distal region of said delivery member including a tubular housing member having proximal and distal regions and a lumen extending therethrough, wherein the proximal region of said tubular housing member is fixedly coupled to said delivery member, a resilient engagement member having proximal and distal ends and a tip member positioned at said engagement member distal end wherein the distal end of said engagement member extends distal to the distal region of said tubular housing member and is positioned within said coupling member aperture, and said tip member engages said engagement portion of said coupling member, an elongate release member having proximal and distal ends and being positioned within the lumen of said delivery member, said release member having a first configuration wherein the distal end of said release member is positioned within said coupling member aperture adjacent said engagement member and in cooperation with said engagement member restricts the uncoupling of said coupling member from said engagement member and a second configuration wherein the distal end of said release member allows the uncoupling of said coupling member from said engagement member, said release member being in said first configuration and being operable between said first and second configurations, and an attachable handle assembly comprising a housing body having first and second ends, a housing lumen extending between said first and second ends and a housing channel positioned between said first and second ends that intersects said housing lumen, and a plunger assembly having a top portion fixedly attached to an elongate shaft member, said shaft member having a shaft lumen and said shaft member being slidably positioned within said housing channel, said handle assembly having a first configuration adapted to receive the proximal region of said delivery member wherein the position of said shaft lumen and said housing lumen are substantially coaxial and a second configuration wherein the position of said shaft lumen and said housing lumen are substantially offset, said handle assembly being operable between said first and second configuration, such that when said handle assembly is in said first configuration and said proximal region of said delivery member is positioned within said housing lumen and extending through said shaft lumen, operating said handle assembly from said first configuration to said second configuration causes said release member to move from its first configuration to its second configuration.

32. A medical implant deployment system according to claim 31 wherein said implant is an embolic coil.

33. A medical implant deployment system according to claim 32 wherein said housing channel and said housing lumen are substantially perpendicular.

34. A medical implant deployment system according to claim 32 wherein said shaft member includes a centering tab that engages with said housing body when said handle assembly is in said first configuration.

35. A medical implant deployment system according to claim 32 wherein said housing body includes first and second contours.

36. A medical implant deployment system according to claim 32 wherein said housing body includes a housing lumen taper adjacent said first end.

37. A medical implant deployment system according to claim 32 wherein said housing body includes a housing lumen taper adjacent said second end.

38. A medical implant deployment system according to claim 32 wherein said release member proximal end includes a resilient spring member having proximal and distal ends wherein said spring member proximal end is coupled to said release member proximal end and the distal end of said spring member is coupled to the proximal region of said delivery member.

39. A medical implant deployment system according to claim 31 wherein said housing channel and said housing lumen are substantially perpendicular.

40. A medical implant deployment system according to claim 31 wherein said shaft member includes a centering tab that engages with said housing body when said handle assembly is in said first configuration.

41. A medical implant deployment system according to claim 31 wherein said housing body includes first and second contours.

42. A medical implant deployment system according to claim 31 wherein said housing body includes a housing lumen taper adjacent said first end.

43. A medical implant deployment system according to claim 31 wherein said housing body includes a housing lumen taper adjacent said second end.

44. A medical implant deployment system according to claim 31 wherein said release member proximal end includes a resilient spring member having proximal and distal ends wherein said spring member proximal end is coupled to said release member proximal end and the distal end of said spring member is coupled to the proximal region of said delivery member.

* * * * *